(12) United States Patent
Bailey et al.

(10) Patent No.: US 9,600,030 B2
(45) Date of Patent: Mar. 21, 2017

(54) SYSTEMS, ARTICLES, AND METHODS FOR ELASTIC ELECTRICAL CABLES AND WEARABLE ELECTRONIC DEVICES EMPLOYING SAME

(71) Applicant: Thalmic Labs Inc., Kitchener (CA)

(72) Inventors: Matthew Bailey, Kitchemer (CA); Stephen E. Orzel, Hamilton (CA)

(73) Assignee: THALMIC LABS INC., Kitchener (CA)

( * ) Notice: Subject to any disclaimer, the term of this patent is extended or adjusted under 35 U.S.C. 154(b) by 12 days.

(21) Appl. No.: 14/621,044

(22) Filed: Feb. 12, 2015

(65) Prior Publication Data

US 2015/0234426 A1  Aug. 20, 2015

Related U.S. Application Data

(60) Provisional application No. 62/031,651, filed on Jul. 31, 2014, provisional application No. 61/940,048, filed on Feb. 14, 2014.

(51) Int. Cl.
*G06F 1/16* (2006.01)
*A61B 5/0492* (2006.01)
(Continued)

(52) U.S. Cl.
CPC ............ *G06F 1/163* (2013.01); *A61B 5/0492* (2013.01); *A61B 5/6831* (2013.01); *H05K 1/147* (2013.01);
(Continued)

(58) Field of Classification Search
CPC ........ G06F 3/033; G06F 3/017; G06F 3/0484; H04M 1/00
(Continued)

(56) References Cited

U.S. PATENT DOCUMENTS 1,411,995 A   4/1922 Dull
3,620,208 A  11/1971 Higley et al.
(Continued)

FOREIGN PATENT DOCUMENTS

DE   44 12 278 A1   10/1995
EP   0 301 790 A2   2/1989
(Continued)

OTHER PUBLICATIONS

Costanza et al., "EMG as a Subtle Input Interface for Mobile Computing," Mobile HCI 2004, LNCS 3160, edited by S. Brewster and M. Dunlop, Springer-Verlag Berlin Heidelberg, pp. 426-430, 2004.

(Continued)

Primary Examiner — Hung Duong
(74) Attorney, Agent, or Firm — Seed IP Law Group LLP

(57) ABSTRACT

Systems, articles, and methods for elastic electrical cables are described. An elastic electrical cable includes a molded band of elastomer with a length that follows a tortuous path including a number of semi-rigidly set changes in direction. The elastomer band is formed by an overmolding process to enclose or at least partially contain a flexible printed circuit board, with various access points provided to electrically couple to/from the flexible printed circuit board. An annular wearable electric device employing at least one such elastic electrical cable as an adaptive coupler that simultaneously provides both electrically conductive coupling and adaptive physical coupling is described. Methods of preparing/manufacturing such elastic electrical cables are also described.

28 Claims, 8 Drawing Sheets

(51) Int. Cl.
  *A61B 5/00* (2006.01)
  *H05K 1/14* (2006.01)
  *H05K 1/02* (2006.01)

(52) U.S. Cl.
  CPC ... *A61B 2562/164* (2013.01); *A61B 2562/166* (2013.01); *A61B 2562/222* (2013.01); *H05K 1/0283* (2013.01)

(58) Field of Classification Search
  USPC ....... 600/372, 379, 383, 388, 301, 546, 391, 600/545, 595, 300, 587, 395; 345/156, 345/158, 173; 455/575.1, 575.2, 575.3, 455/90.1, 550.1, 556.1, 556.2; 324/658, 324/663
  See application file for complete search history.

(56) References Cited

U.S. PATENT DOCUMENTS

| | | |
|---|---|---|
| 3,880,146 A | 4/1975 | Everett et al. |
| 4,602,639 A | 7/1986 | Hoogendoorn et al. |
| 4,817,064 A | 3/1989 | Milles |
| 5,003,978 A | 4/1991 | Dunseath, Jr. |
| D322,227 S | 12/1991 | Warhol |
| 5,081,852 A | 1/1992 | Cox |
| 5,251,189 A | 10/1993 | Thorp |
| D348,660 S | 7/1994 | Parsons |
| 5,445,869 A | 8/1995 | Ishikawa et al. |
| 5,482,051 A | 1/1996 | Reddy et al. |
| 5,605,059 A | 2/1997 | Woodward |
| 5,683,404 A | 11/1997 | Johnson |
| 6,032,530 A | 3/2000 | Hock |
| 6,184,847 B1 | 2/2001 | Fateh et al. |
| 6,238,338 B1 | 5/2001 | DeLuca et al. |
| 6,244,873 B1 | 6/2001 | Hill et al. |
| 6,377,277 B1 | 4/2002 | Yamamoto |
| D459,352 S | 6/2002 | Giovanniello |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,720,984 B1 | 4/2004 | Jorgensen et al. |
| 6,743,982 B2 | 6/2004 | Biegelsen et al. |
| 6,807,438 B1 | 10/2004 | Brun Del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,927,343 B2 | 8/2005 | Watanabe et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,086,218 B1 | 8/2006 | Pasach |
| D535,401 S | 1/2007 | Travis et al. |
| 7,173,437 B2 | 2/2007 | Hervieux et al. |
| D543,212 S | 5/2007 | Marks |
| 7,265,298 B2 | 9/2007 | Maghribi et al. |
| 7,271,774 B2 * | 9/2007 | Puuri .................... H01Q 13/10 343/718 |
| 7,333,090 B2 | 2/2008 | Tanaka et al. |
| 7,450,107 B2 | 11/2008 | Radley-Smith |
| 7,558,622 B2 | 7/2009 | Tran |
| 7,596,393 B2 | 9/2009 | Jung et al. |
| 7,618,260 B2 | 11/2009 | Daniel et al. |
| 7,640,007 B2 | 12/2009 | Chen et al. |
| 7,660,126 B2 | 2/2010 | Cho et al. |
| 7,809,435 B1 | 10/2010 | Ettare et al. |
| D643,428 S | 8/2011 | Janky et al. |
| D646,192 S | 10/2011 | Woode |
| 8,054,061 B2 | 11/2011 | Prance et al. |
| D654,622 S | 2/2012 | Hsu |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| D661,613 S | 6/2012 | Demeglio |
| 8,203,502 B1 | 6/2012 | Chi et al. |
| 8,212,859 B2 | 7/2012 | Tang et al. |
| 8,355,671 B2 | 1/2013 | Kramer et al. |
| 8,421,634 B2 | 4/2013 | Tan et al. |
| D682,727 S | 5/2013 | Bulgari |
| 8,447,704 B2 | 5/2013 | Tan et al. |
| 8,467,270 B2 | 6/2013 | Gossweiler, III et al. |
| D689,862 S | 9/2013 | Liu |
| D695,454 S | 12/2013 | Moore |
| 8,624,124 B2 | 1/2014 | Koo et al. |
| D716,457 S | 10/2014 | Brefka et al. |
| D717,685 S | 11/2014 | Bailey et al. |
| 8,912,094 B2 | 12/2014 | Koo et al. |
| 8,922,481 B1 | 12/2014 | Kauffmann et al. |
| 8,971,023 B2 | 3/2015 | Olsson et al. |
| 9,018,532 B2 | 4/2015 | Wesselmann et al. |
| D736,664 S | 8/2015 | Paradise et al. |
| D741,855 S | 10/2015 | Park et al. |
| D742,272 S | 11/2015 | Bailey et al. |
| D742,874 S | 11/2015 | Cheng et al. |
| D743,963 S | 11/2015 | Osterhout |
| D747,714 S | 1/2016 | Erbeus |
| D750,623 S | 3/2016 | Park et al. |
| D751,065 S | 3/2016 | Magi |
| 9,299,248 B2 | 3/2016 | Lake et al. |
| D756,359 S | 5/2016 | Bailey et al. |
| 9,367,139 B2 | 6/2016 | Ataee et al. |
| 9,372,535 B2 | 6/2016 | Bailey et al. |
| 2002/0032386 A1 | 3/2002 | Sackner et al. |
| 2002/0077534 A1 | 6/2002 | DuRousseau |
| 2003/0036691 A1 | 2/2003 | Stanaland et al. |
| 2003/0144586 A1 | 7/2003 | Tsubata |
| 2004/0068409 A1 | 4/2004 | Tanaka et al. |
| 2004/0073104 A1 | 4/2004 | Brun del Re et al. |
| 2004/0194500 A1 | 10/2004 | Rapport |
| 2004/0210165 A1 | 10/2004 | Marmaropoulos et al. |
| 2005/0005637 A1 | 1/2005 | Rapport |
| 2005/0012715 A1 | 1/2005 | Ford |
| 2005/0119701 A1 | 6/2005 | Lauter et al. |
| 2005/0177038 A1 | 8/2005 | Kolpin et al. |
| 2006/0037359 A1 | 2/2006 | Stinespring |
| 2006/0061544 A1 | 3/2006 | Min et al. |
| 2007/0132785 A1 | 6/2007 | Ebersole, Jr. et al. |
| 2008/0136775 A1 | 6/2008 | Conant |
| 2009/0007597 A1 | 1/2009 | Hanevold |
| 2009/0031757 A1 | 2/2009 | Harding |
| 2009/0040016 A1 | 2/2009 | Ikeda |
| 2009/0051544 A1 | 2/2009 | Niknejad |
| 2009/0102580 A1 | 4/2009 | Uchaykin |
| 2009/0189867 A1 | 7/2009 | Krah et al. |
| 2009/0251407 A1 | 10/2009 | Flake et al. |
| 2009/0318785 A1 | 12/2009 | Ishikawa et al. |
| 2009/0326406 A1 | 12/2009 | Tan et al. |
| 2009/0327171 A1 | 12/2009 | Tan et al. |
| 2010/0041974 A1 | 2/2010 | Ting et al. |
| 2010/0280628 A1 | 11/2010 | Sankai |
| 2010/0293115 A1 | 11/2010 | Seyed Momen |
| 2010/0317958 A1 | 12/2010 | Beck et al. |
| 2011/0134026 A1 | 6/2011 | Kang et al. |
| 2011/0166434 A1 | 7/2011 | Gargiulo |
| 2011/0172503 A1 | 7/2011 | Knepper et al. |
| 2012/0029322 A1 | 2/2012 | Wartena et al. |
| 2012/0051005 A1 | 3/2012 | Vanfleteren et al. |
| 2012/0101357 A1 | 4/2012 | Hoskuldsson et al. |
| 2012/0157789 A1 | 6/2012 | Kangas et al. |
| 2012/0165695 A1 | 6/2012 | Kidmose et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0265090 A1 | 10/2012 | Fink et al. |
| 2012/0293548 A1 | 11/2012 | Perez et al. |
| 2012/0302858 A1 | 11/2012 | Kidmose et al. |
| 2013/0005303 A1 | 1/2013 | Song et al. |
| 2013/0027341 A1 | 1/2013 | Mastandrea |
| 2013/0127708 A1 | 5/2013 | Jung et al. |
| 2013/0165813 A1 | 6/2013 | Chang et al. |

(56) References Cited

U.S. PATENT DOCUMENTS

| | | | |
|---|---|---|---|
| 2013/0191741 A1 | 7/2013 | Dickinson et al. | |
| 2013/0198694 A1 | 8/2013 | Rahman et al. | |
| 2013/0265229 A1 | 10/2013 | Forutanpour et al. | |
| 2013/0265437 A1 | 10/2013 | Thörn et al. | |
| 2013/0312256 A1 | 11/2013 | Wesselmann et al. | |
| 2013/0317648 A1 | 11/2013 | Assad | |
| 2014/0020945 A1 | 1/2014 | Hurwitz et al. | |
| 2014/0028546 A1 | 1/2014 | Jeon et al. | |
| 2014/0049417 A1 | 2/2014 | Abdurrahman et al. | |
| 2014/0194062 A1 | 7/2014 | Palin et al. | |
| 2014/0198034 A1 | 7/2014 | Bailey et al. | |
| 2014/0198035 A1 | 7/2014 | Bailey et al. | |
| 2014/0236031 A1 | 8/2014 | Banet et al. | |
| 2014/0240103 A1 | 8/2014 | Lake et al. | |
| 2014/0249397 A1 | 9/2014 | Lake et al. | |
| 2014/0299362 A1 | 10/2014 | Park et al. | |
| 2014/0334083 A1 | 11/2014 | Bailey | |
| 2014/0337861 A1 | 11/2014 | Chang et al. | |
| 2014/0349257 A1 | 11/2014 | Connor | |
| 2014/0354528 A1 | 12/2014 | Laughlin et al. | |
| 2014/0354529 A1 | 12/2014 | Laughlin et al. | |
| 2014/0364703 A1 | 12/2014 | Kim et al. | |
| 2015/0011857 A1 | 1/2015 | Henson et al. | |
| 2015/0025355 A1 | 1/2015 | Bailey et al. | |
| 2015/0051470 A1 | 2/2015 | Bailey et al. | |
| 2015/0057770 A1 | 2/2015 | Bailey et al. | |
| 2015/0065840 A1 | 3/2015 | Bailey | |
| 2015/0084860 A1 | 3/2015 | Aleem et al. | |
| 2015/0109202 A1 | 4/2015 | Ataee et al. | |
| 2015/0124566 A1 | 5/2015 | Lake et al. | |
| 2015/0141784 A1 | 5/2015 | Morun et al. | |
| 2015/0148641 A1 | 5/2015 | Morun et al. | |
| 2015/0160621 A1 | 6/2015 | Yilmaz | |
| 2015/0237716 A1 | 8/2015 | Su et al. | |
| 2015/0261306 A1 | 9/2015 | Lake | |
| 2015/0277575 A1 | 10/2015 | Ataee et al. | |
| 2015/0296553 A1 | 10/2015 | DiFranco et al. | |
| 2015/0325202 A1 | 11/2015 | Lake et al. | |
| 2015/0370333 A1 | 12/2015 | Ataee et al. | |
| 2016/0020500 A1 | 1/2016 | Matsuda | |
| 2016/0150636 A1 | 5/2016 | Otsubo | |
| 2016/0156762 A1 | 6/2016 | Bailey et al. | |
| 2016/0199699 A1* | 7/2016 | Klassen | A63B 22/16 482/146 |
| 2016/0309249 A1* | 10/2016 | Wu | H04R 1/105 |

FOREIGN PATENT DOCUMENTS

| | | |
|---|---|---|
| JP | 2009-50679 A | 3/2009 |
| KR | 20120094870 A | 8/2012 |
| KR | 20120097997 A | 9/2012 |
| WO | 2011/070554 A2 | 6/2011 |

OTHER PUBLICATIONS

Costanza et al., "Toward Subtle Intimate Interfaces for Mobile Devices Using an EMG Controller," CHI 2005, Proceedings of the SIGCHI Conference on Human Factors in Computing Systems, pp. 481-489, 2005.

Ghasemzadeh et al., "A Body Sensor Network With Electromyogram and Inertial Sensors: Multimodal Interpretation of Muscular Activities," IEEE Transactions on Information Technology in Biomedicine, vol. 14, No. 2, pp. 198-206, Mar. 2010.

Gourmelon et al., "Contactless sensors for Surface Electromyography," Proceedings of the 28th IEEE EMBS Annual International Conference, New York City, NY, Aug. 30-Sep. 3, 2006, pp. 2514-2517.

International Search Report and Written Opinion, mailed May 16, 2014, for corresponding International Application No. PCT/US2014/017799, 9 pages.

International Search Report and Written Opinion, mailed Aug. 21, 2014, for corresponding International Application No. PCT/US2014/037863, 10 pages.

International Search Report and Written Opinion, mailed Nov. 21, 2014, for corresponding International Application No. PCT/US2014/052143, 9 pages.

International Search Report and Written Opinion, mailed Feb. 27, 2015, for corresponding International Application No. PCT/US2014/067443, 10 pages.

International Search Report and Written Opinion, mailed May 27, 2015, for corresponding International Application No. PCT/US2015/015675, 9 pages.

Morris et al., "Emerging Input Technologies for Always-Available Mobile Interaction," *Foundations and Trends in Human-Computer Interaction* 4(4):245-316, 2010. (74 total pages).

Naik et al., "Real-Time Hand Gesture Identification for Human Computer Interaction Based on ICA of Surface Electromyogram," IADIS International Conference Interfaces and Human Computer Interaction 2007, 8 pages.

Picard et al., "Affective Wearables," Proceedings of the IEEE $1^{st}$ International Symposium on Wearable Computers, ISWC, Cambridge, MA, USA, Oct. 13-14, 1997, pp. 90-97.

Rekimoto, "GestureWrist and GesturePad: Unobtrusive Wearable Interaction Devices," ISWC '01 Proceedings of the $5^{th}$ IEEE International Symposium on Wearable Computers, 2001, 7 pages.

Saponas et al., "Making Muscle-Computer Interfaces More Practical," CHI 2010, Atlanta, Georgia, USA, Apr. 10-15, 2010, 4 pages.

Sato et al., "Touche: Enhancing Touch Interaction on Humans, Screens, Liquids, and Everyday Objects," CHI' 12, May 5-10, 2012, Austin, Texas.

Ueno et al., "A Capacitive Sensor System for Measuring Laplacian Electromyogram through Cloth: A Pilot Study," Proceedings of the $29^{th}$ Annual International Conference of the IEEE EMBS, Cite Internationale, Lyon, France, Aug. 23-26, 2007.

Ueno et al., "Feasibility of Capacitive Sensing of Surface Electromyographic Potential through Cloth," *Sensors and Materials* 24(6):335-346, 2012.

Xiong et al., "A Novel HCI based on EMG and IMU," Proceedings of the 2011 IEEE International Conference on Robotics and Biomimetics, Phuket, Thailand, Dec. 7-11, 2011, 5 pages.

Zhang et al., "A Framework for Hand Gesture Recognition Based on Accelerometer and EMG Sensors," IEEE Transactions on Systems, Man, and Cybernetics—Part A: Systems and Humans, vol. 41, No. 6, pp. 1064-1076, Nov. 2011.

Xu et al., "Hand Gesture Recognition and Virtual Game Control Based on 3D Accelerometer and EMG Sensors," Proceedings of the 14th international conference on Intelligent user interfaces, Sanibel Island, Florida, Feb. 8-11, 2009, 401-406.

Communication pursuant to Rule 164(1) EPC, dated Sep. 30, 2016, for corresponding EP Application No. 14753949.8, 7 pages.

\* cited by examiner

SYSTEMS, ARTICLES, AND METHODS FOR ELASTIC ELECTRICAL CABLES AND WEARABLE ELECTRONIC DEVICES EMPLOYING SAME

BACKGROUND

Technical Field

The present systems, articles, and methods generally relate to elastic electrical cables, including manufacturing methods thereof and annular wearable electronic devices that employ one or more elastic electrical cable(s) in order to realize a variable circumference.

Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

The potential users of a wearable electronic device may come in many different shapes and sizes. To address this, either a unique wearable electronic device must be designed and built (e.g., customized) for each individual user type, or an individual device must be able to accommodate a variety of different user forms. For some devices this is simply a matter of comfort for the user, whereas for other devices the operation/performance is affected by the fit between the device and the user. For example, the operation/performance of a wearable electronic device that employs sensors responsive to (i.e., to detect, measure, or sense) inputs from a user may be influenced by how the fit between the device and the user causes the sensors to be oriented on the user's form.

The same wearable electronic device may operate/perform differently when worn by two differently shaped users, or even when movement or activity causes variations in the form when worn by a single user. Such operation/performance inconsistencies can result in a poor user experience and are clearly undesirable. It is impractical to design and build a customized wearable electronic device for each user, thus there is a need in the art for wearable electronic devices that are better able to accommodate variations in user form.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs from a user and the wearable electronic device may transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to HCIs, but may also be applied to any other form of human-electronics interface.

Electromyography Devices

Electromyography ("EMG") is a process for detecting and processing the electrical signals generated by muscle activity. EMG devices employ EMG sensors that are responsive to the range of electrical potentials (typically $\mu$V-mV) involved in muscle activity. EMG signals may be used in a wide variety of applications, including: medical monitoring and diagnosis, muscle rehabilitation, exercise and training, prosthetic control, and even in controlling functions of electronic devices.

BRIEF SUMMARY

An annular wearable electronic device having a circumference that is variable in a dimension may be summarized as including: a first pod structure positioned at least approximately on the circumference of the annular wearable electronic device, wherein the first pod structure includes electric circuitry; a second pod structure positioned at least approximately on the circumference of the annular wearable electronic device, wherein the second pod structure includes electric circuitry and wherein the first pod structure and the second pod structure are physically separated from one another by a first distance at least approximately along the circumference of the annular wearable electronic device; and a first adaptive coupler positioned at least approximately on the circumference of the annular wearable electronic device, wherein the first adaptive coupler provides both electrically conductive coupling and adaptive physical coupling between the first pod structure and the second pod structure, and wherein the first adaptive coupler comprises: at least a first electrically conductive pathway that is electrically conductively coupled to both the electric circuitry of the first pod structure and the electric circuitry of the second pod structure; and a first elastomer band that is physically coupled to both the first pod structure and the second pod structure, wherein at least a portion of the first electrically conductive pathway extends through an inner volume of the first elastomer band, and wherein a length of the first elastomer band that couples in between the first pod structure and the second pod structure is greater than the first distance and includes at least one semi-rigidly set change in direction. When not worn by a user, the dimension of the circumference of the annular wearable electronic device may be a minimum value with the first adaptive coupler in an unstretched state; and when worn by the user, the dimension of the circumference of the annular wearable electronic device may be increased to encircle a portion of the user with the first adaptive coupler in a stretched state, the stretched state of the first adaptive coupler achieved by a change in an angle of the at least one semi-rigidly set change in direction in the length of the first elastomer band that couples in between the first pod structure and the second pod structure.

The first elastomer band may include an overmold portion over the at least a portion of the first electrically conductive pathway that extends through the inner volume of the first elastomer band. The first elastomer band may comprise: a first longitudinal section of elastomer having a recess that is sized and dimensioned to receive the at least a portion of the first electrically conductive pathway that extends through the inner volume of the first elastomer band, wherein the first longitudinal section of elastomer includes the number of semi-rigidly set changes in direction; and a second longitudinal section of overmold elastomer over at least a portion of the recess of the first longitudinal section of elastomer to define the inner volume of the first elastomer band.

The first electrically conductive pathway may include at least one electrically conductive trace carried by a flexible substrate.

The annular wearable electronic device may further include a third pod structure positioned at least approximately on the circumference of the annular wearable electronic device, where: the third pod structure includes electric circuitry; the second pod structure and the third pod structure are physically separated from one another by a second distance at least approximately along the circumference of the annular wearable electronic device; the first adaptive coupler provides electrically conductive coupling and adaptive physical coupling between the second pod structure and the third pod structure; the first adaptive coupler further comprises at least a second electrically conductive pathway that is electrically conductively coupled to the electric circuitry of the second pod structure and to the electric circuitry of the third pod structure; and the first elastomer band is physically coupled to both the second pod structure and the third pod structure, wherein at least a portion of the second electrically conductive pathway extends through an inner volume of the first elastomer band, and wherein a length of the first elastomer band that couples in between the second pod structure and the third pod structure is greater than the second distance and includes at least one semi-rigidly set change in direction.

The annular wearable electronic device may further include: a third pod structure positioned at least approximately on the circumference of the annular wearable electronic device, wherein the third pod structure includes electric circuitry and wherein the second pod structure and the third pod structure are physically separated from one another by a second distance at least approximately along the circumference of the annular wearable electronic device; and a second adaptive coupler positioned at least approximately on the circumference of the annular wearable electronic device, wherein the second adaptive coupler provides both electrically conductive coupling and adaptive physical coupling between the second pod structure and the third pod structure, and wherein the second adaptive coupler comprises: at least a second electrically conductive pathway that is electrically conductively coupled to both the electric circuitry of the third pod structure and the electric circuitry of the second pod structure; and a second elastomer band that is physically coupled to both the second pod structure and the third pod structure, wherein at least a portion of the second electrically conductive pathway extends through an inner volume of the second elastomer band, and wherein a length of the second elastomer band that couples in between the second pod structure and the third pod structure is greater than the second distance and includes at least one semi-rigidly set change in direction.

The length of the first elastomer band that couples in between the first pod structure and the second pod structure may follow a tortuous path that includes the at least one semi-rigidly set change in direction.

The annular wearable electronic device may further include a second elastomer band that is physically coupled to both the first pod structure and the second pod structure, wherein a length of the second elastomer band that couples in between the first pod structure and the second pod structure is greater than the first distance and includes at least one semi-rigidly set change in direction.

An elastic electrical cable may be summarizes as including: a flexible printed circuit board including at least one electrically conductive trace carried on a flexible substrate; and an elastomer band, wherein at least a portion of the flexible printed circuit board extends through an inner volume of the elastomer band, and wherein a length of the elastomer band follows a tortuous path that includes a number of semi-rigidly set changes in direction.

The elastomer band may include an overmold portion over the at least a portion of the flexible printed circuit board that extends through the inner volume of the elastomer band. The elastomer band may comprise: a first longitudinal section of elastomer having a recess that is sized and dimensioned to receive the at least a portion of the flexible printed circuit board, wherein the first longitudinal section of elastomer includes the number of semi-rigidly set changes in direction; and a second longitudinal section of overmold elastomer over at least a portion of the first longitudinal section of elastomer to define the inner volume of the band.

A first end of the flexible printed circuit board may be positioned proximate a first end of the elastomer band and a second end of the flexible printed circuit board may positioned proximate a second end of the elastomer band, with the elastic electrical cable further including: a first electrical connector electrically conductively coupled to the first end of the flexible printed circuit board; and a second electrical connector electrically conductively coupled to the second end of the flexible printed circuit board.

The elastomer band may include an impression from an injection gate, the impression positioned at one of the number of semi-rigidly set changes in direction in correspondence with the position of the injection gate in a mold used to form the elastomer band. The elastic electrical cable may further include an adhesive layer that adheres a first surface of the flexible printed circuit board to an inner surface of the elastomer band.

A method of fabricating an elastic electrical cable, wherein the elastic electrical cable comprises a flexible printed circuit board and an elastomer band, and wherein at least a portion of the flexible printed circuit board extends through an inner volume of the elastomer band, may be summarizes as including: molding a first longitudinal section of the elastomer band to include a recessed surface and a number of semi-rigid changes in direction; depositing the flexible printed circuit board against the recessed surface of the first longitudinal section of the elastomer band; and overmolding at least a portion of the flexible printed circuit board and at least a portion of the first longitudinal section of the elastomer band with a second longitudinal section of the elastomer band to enclose at least a portion of the flexible printed circuit board within the inner volume of the elastomer band.

Depositing the flexible printed circuit board against the recessed surface of the first longitudinal section of the elastomer band may includes: bending the flexible printed circuit board to match the number of semi-rigid changes in direction in the first longitudinal section of the elastomer band; and positioning the bent flexible printed circuit board against the recessed surface of the first longitudinal section of the elastomer band.

Molding a first longitudinal section of the elastomer band may include molding the first longitudinal section of the elastomer band in a first mold. Overmolding at least a portion of the flexible printed circuit board and at least a portion of the first longitudinal section of the elastomer band with a second longitudinal section of the elastomer band may include overmolding at least a portion of the flexible printed circuit board and at least a portion of the first longitudinal section of the elastomer band with a second longitudinal section of the elastomer band in a second mold. The method may further include: removing the first longitudinal section of the elastomer band from the first mold; and depositing the first longitudinal section of the elastomer band against an inner surface of the second mold, wherein depositing the flexible printed circuit board against the recessed surface of the first longitudinal section of the elastomer band includes depositing the flexible printed circuit board against the recessed surface of the first longitudinal section of the elastomer band while the first longitudinal section of the elastomer band is against the inner surface of the second mold. The first mold may be sized and dimensioned to accommodate substantially 0% shrinkage of the first longitudinal section of the elastomer band, and: molding a first longitudinal section of the elastomer band may include molding a first longitudinal section of the elastomer band to accommodate substantially 0% shrinkage of the first longitudinal section of the elastomer band; and depositing the first longitudinal section of the elastomer band against an inner surface of the second mold may include stretching the first longitudinal section of the elastomer band against the inner surface of the second mold. The second mold may be sized and dimensioned to accommodate substantially 0% shrinkage of the second longitudinal section of the elastomer band, and overmolding at least a portion of the flexible printed circuit board and at least a portion of the first longitudinal section of the elastomer band with a second longitudinal section of the elastomer band may include overmolding at least a portion of the flexible printed circuit board and at least a portion of the first longitudinal section of the elastomer band with a second longitudinal section of the elastomer band to accommodate substantially 0% shrinkage of the second longitudinal section of the elastomer band while the first longitudinal section of the elastomer band is stretched against the inner surface of the second mold.

The method may further include depositing an adhesive on a first surface of the flexible printed circuit board, and depositing the flexible printed circuit board against the recessed surface of the first longitudinal section of the elastomer band may include depositing the first surface of the flexible printed circuit board against the recessed surface of the first longitudinal section of the elastomer band after depositing the adhesive on the first surface of the flexible printed circuit board. The adhesive may include a pressure sensitive adhesive, and the method may include pressing the flexible printed circuit board against the recessed surface of the first longitudinal section of the elastomer band, wherein pressing the flexible printed circuit board against the recessed surface of the first longitudinal section of the elastomer band activates the pressure sensitive adhesive and adheres the first surface of the flexible printed circuit board to the recessed surface of the first longitudinal section of the elastomer band.

Overmolding at least a portion of the flexible printed circuit board and at least a portion of the first longitudinal section of the elastomer band with a second longitudinal section of the elastomer band may include injecting an elastomer material into a mold through a first gate, the first gate positioned at a location of a first one of the number of semi-rigid changes in direction in the first longitudinal section of the elastomer band. Overmolding at least a portion of the flexible printed circuit board and at least a portion of the first longitudinal section of the elastomer band with a second longitudinal section of the elastomer band may include injecting the elastomer material into the mold through a plurality of additional gates, each gate in the plurality of additional gates positioned at a location of a respective one of the number of semi-rigid changes in direction in the first longitudinal section of the elastomer band.

An elastic electrical cable that includes a flexible printed circuit board and an elastomer band may be prepared by a process that may be summarized as including: molding a first longitudinal section of the elastomer band to include a recessed surface and a number of semi-rigid changes in direction; depositing the flexible printed circuit board onto the recessed surface of the first longitudinal section of the elastomer band; and overmolding the flexible printed circuit board and at least a portion of the first longitudinal section of the elastomer band with a second longitudinal section of the elastomer band to enclose at least a portion of the flexible printed circuit board within an inner volume of the elastomer band.

A method of fabricating an electric device, wherein the electric device comprises at least an electrically conductive pathway and an elastomer band, and wherein at least a portion of the electrically conductive pathway extends through an inner volume of the elastomer band, may be summarized as including: molding a first longitudinal section of the elastomer band in a first mold that is sized and dimensioned to accommodate substantially 0% shrinkage of the first longitudinal section of the elastomer band; removing the first longitudinal section of the elastomer band from the first mold; stretching the first longitudinal section of the elastomer band against an inner surface of a second mold; depositing the electrically conductive pathway against the first longitudinal section of the elastomer band while the first longitudinal section of the elastomer band is stretched against the inner surface of the second mold; and overmolding at least a portion of the electrically conductive pathway and at least a portion of the first longitudinal section of the elastomer band with a second longitudinal section of the elastomer band in a second mold to enclose at least a portion of the electrically conductive pathway within the inner volume of the elastomer band. The second mold may be sized and dimensioned to accommodate substantially 0% shrinkage of the second longitudinal section of the elastomer band, and overmolding at least a portion of the electrically conductive pathway and at least a portion of the first longitudinal section of the elastomer band with a second longitudinal section of the elastomer band may include overmolding at least a portion of the electrically conductive pathway and at least a portion of the first longitudinal section of the elastomer band with a second longitudinal section of the elastomer band to accommodate substantially 0% shrinkage of the second longitudinal section of the elastomer band while the first longitudinal section of the elastomer band is stretched against the inner surface of the second mold.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
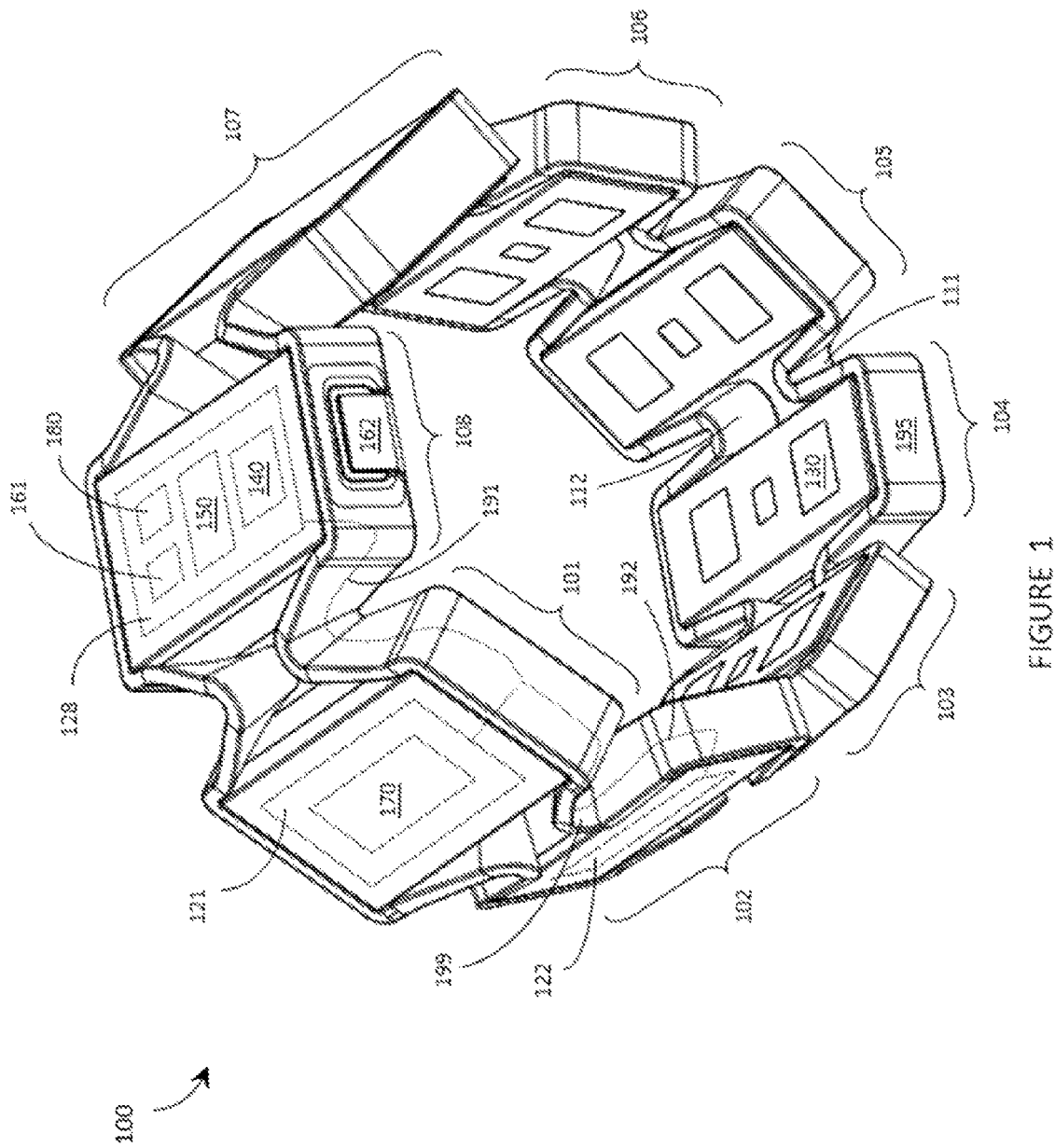
FIG. 1 is a perspective view of an exemplary annular wearable electronic device that incorporates two elastic electrical cables as adaptive couplers in order to achieve a variable circumference that accommodates a variety of different user forms in accordance with the present systems, articles, and methods.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with portable electronic devices and/or electrical cables have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for elastic electrical cables and the manufacturing thereof. In an exemplary application, a wearable electronic device is described that employs one or more such elastic electrical cable(s) to realize a variable circumference that accommodates different user forms. Specifically, at least one elastic electrical cable is used as an "adaptive coupler" that simultaneously provides both electrically conductive coupling and adaptive physical coupling between components of the wearable electronic device. Throughout this specification and the appended claims, the term "elastic electrical cable" generally refers to an electrical cable having elastic properties that render the cable stretchable, expandable, pliable, or otherwise variable in at least one dimension (e.g., length) subject to restorative forces, and the term "adaptive coupler" generally refers to a device or structure that provides flexible, elastic, resilient, adjustable, modifiable, extendable, extensible, or otherwise "adaptive" physical coupling between at least two points/objects. Adaptive physical coupling is physical coupling between at least two points/objects that permits limited motion of the two points/objects relative to one another. The present systems, articles, and methods describe (among other things) wearable electronic devices that employ elastic electrical cables as adaptive couplers in order to simultaneously provide electrically conductive coupling and adaptive physical coupling between two points/objects of the wearable electronic device through a single coupling structure.

Throughout this specification and the appended claims, the term "form" as in "user form" is used to generally describe the physical properties of the portion of a user upon which a wearable electronic device is worn. The physical properties may include any characteristic that can influence the fit and/or operation/performance of the wearable electronic device, including but not limited to: shape, size, geometry, topography, mass, volume, density, composition, elasticity, etc.

FIG. 1 is a perspective view of an exemplary annular wearable electronic device 100 that incorporates two adaptive couplers 111 and 112 in order to achieve a variable circumference that accommodates a variety of different user forms in accordance with the present systems, articles, and methods. Exemplary annular wearable electronic device 100 may, for example, form part of a human-electronics interface. Exemplary annular wearable electronic device 100 is an armband designed to be worn on the forearm of a user, though a person of skill in the art will appreciate that the teachings described herein may readily be applied in wearable electronic devices (annular or otherwise) designed to be worn elsewhere on the body of the user, including without limitation: on the upper arm, wrist, hand, finger, leg, foot, torso, or neck of the user.

Throughout this specification and the appended claims, the term "circumference" is used in an approximate sense to generally describe an enclosing boundary (e.g., perimeter) of a curved geometric figure, for example a circle, annulus, or an oval, but is in no way intended to limit the figure being described to a precisely circular geometry. Likewise, the term "annular" is not limited to circular geometries but is instead used in an approximate sense to generally describe a curved geometric figure with mass distributed around its circumference and an opening through its volume.

Device 100 includes a set of eight pod structures 101, 102, 103, 104, 105, 106, 107, and 108 that form physically coupled links of the wearable electronic device 100. Each pod structure in the set of eight pod structures 101, 102, 103, 104, 105, 106, 107, and 108 is positioned adjacent at least one other pod structure in the set of pod structures at least approximately on the circumference of the annular wearable electronic device 100. More specifically, each pod structure in the set of eight pod structures 101, 102, 103, 104, 105, 106, 107, and 108 is positioned adjacent and in between two other pod structures in the set of eight pod structures such that the set of pod structures forms a circumference or perimeter of an annular or closed loop (e.g., closed surface) configuration. For example, pod structure 101 is positioned adjacent and in between pod structures 102 and 108 at least approximately on a circumference or perimeter of the annular or closed loop configuration of pod structures, pod structure 102 is positioned adjacent and in between pod structures 101 and 103 at least approximately on the circumference or perimeter of the annular or closed loop configuration, pod structure 103 is positioned adjacent and in between pod structures 102 and 104 at least approximately on the circumference or perimeter of the annular or closed loop configuration, and so on. Each of pod structures 101, 102, 103, 104, 105, 106, 107, and 108 is adaptively physically coupled to the two adjacent pod structures by two adaptive couplers 111 and 112. For example, pod structure 101 is adaptively physically coupled to both pod structure 108 and pod structure 102 by adaptive couplers 111 and 112. The set of eight pod structures may be physically bound in the annular or closed loop configuration by one or more extended adaptive coupler(s) 111 and/or 112 that couple(s) over, across, or through all pod structures in series or by multiple individual adaptive couplers that couple between adjacent pairs of pod structures or between groups of adjacent pairs of pod structures. Device 100 is depicted in FIG. 1 with two adaptive couplers 111, 112, each positioned at least approximately on the circumference of annular wearable electronic device 100 and each providing serial adaptive physical coupling between all of the pod structures in the set of eight pod structures 101, 102, 103, 104, 105, 106, 107, and 108.

Throughout this specification and the appended claims, the term "pod structure" is used to refer to an individual link, segment, pod, section, structure, component, etc. of a wearable electronic device. For the purposes of the present systems, articles, and methods, an "individual link, segment, pod, section, structure, component, etc." (i.e., a "pod structure") of a wearable electronic device is characterized by its ability to be moved or displaced relative to another link, segment, pod, section, structure component, etc. of the wearable electronic device. For example, pod structures 101 and 102 of device 100 can each be moved or displaced relative to one another within the constraints imposed by the adaptive couplers 111, 112 providing adaptive physical coupling therebetween. The desire for pod structures 101 and 102 to be movable/displaceable relative to one another specifically arises because device 100 is a wearable electronic device that advantageously accommodates the movements of a user and/or different user forms.

Device 100 includes eight pod structures 101, 102, 103, 104, 105, 106, 107, and 108 that form physically coupled links thereof. The number of pod structures included in a wearable electronic device is dependent on at least the nature, function(s), and design of the wearable electronic device, and the present systems, articles, and methods may be applied to any wearable electronic device employing any number of pod structures, including wearable electronic devices employing more than eight pod structures and wearable electronic devices employing fewer than eight pod structures (e.g., at least two pod structures, such as three or more pod structures).

Wearable electronic devices employing pod structures (e.g., device 100) are used herein as exemplary wearable electronic device designs, while the present systems, articles, and methods may be applied to wearable electronic devices that do not employ pod structures (or that employ any number of pod structures). Thus, throughout this specification, descriptions relating to pod structures (e.g., functions and/or components of pod structures) should be interpreted as being applicable to any wearable electronic device design, even wearable electronic device designs that do not employ pod structures (except in cases where a pod structure is specifically recited in a claim).

In exemplary device 100 of FIG. 1, each of pod structures 101, 102, 103, 104, 105, 106, 107, and 108 comprises a respective housing having a respective inner volume. Each housing may be formed of substantially rigid material and may be optically opaque. Throughout this specification and the appended claims, the term "rigid" as in, for example, "substantially rigid material," is used to describe a material that has an inherent resiliency, i.e., a tendency to maintain or restore its shape and resist malformation/deformation under the moderate stresses and strains typically encountered by a wearable electronic device.

Details of the components contained within the housings (i.e., within the inner volumes of the housings) of pod structures 101, 102, 103, 104, 105, 106, 107, and 108 are not visible in FIG. 1. To facilitate descriptions of exemplary device 100, some internal components are depicted by dashed lines in FIG. 1 to indicate that these components are contained in the inner volume(s) of housings and may not normally be actually visible in the view depicted in FIG. 1, unless a transparent or translucent material is employed to form the housings. For example, any or all of pod structures 101, 102, 103, 104, 105, 106, 107, and/or 108 may include electric circuitry (i.e., electrical and/or electronic circuitry). In FIG. 1, a first pod structure 101 is shown containing electric circuitry 121 (i.e., electric circuitry 121 is contained in the inner volume of the housing of pod structure 101), a second pod structure 102 is shown containing electric circuitry 122, and a third pod structure 108 is shown containing electric circuitry 128. The electric circuitry in any or all pod structures may be communicatively coupled to the electric circuitry in at least one other pod structure by at least one communicative pathway (e.g., by at least one electrically conductive pathway and/or by at least one optical pathway). In accordance with the present systems, articles, and methods, such communicative pathways may be carried by, carried on, or carried within one or more adaptive couplers. For example, adaptive coupler 111 of device 100 is an elastic electrical cable comprising an elastomer band that contains (i.e., enclosed within an inner volume thereof) electrically conductive pathways that provide communicative coupling between various ones of pod structures 101, 102, 103, 104, 105, 106, 107, and/or 108. Communicative coupling between electric circuitries of pod structures in device 100 may advantageously include systems, articles, and methods for stretchable printed circuit boards as described in U.S. Provisional Patent Application Ser. No. 61/872,569 (now U.S. Non-Provisional patent application Ser. No. 14/471,982) and/or systems, articles, and methods for signal routing as described in U.S. Provisional Patent Application Ser. No. 61/866,960 (now U.S. Non-Provisional patent application Ser. No. 14/461,044), both of which are incorporated by reference herein in their entirety.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings, magnetic couplings, and/or optical couplings.

Each individual pod structure within a wearable electronic device may perform a particular function, or particular functions. For example, in device 100, each of pod structures 101, 102, 103, 104, 105, 106, and 107 includes a respective sensor 130 (only one called out in FIG. 1 to reduce clutter) responsive to (i.e., to detect) input signals from a user. In response to detecting input signals from the user, sensor 130 provides electrical signals. Because each of pod structures 101, 102, 103, 104, 105, 106, and 107 includes a respective sensor 130, each may be referred to as a respective "sensor pod." Throughout this specification and the appended claims, the term "sensor pod" is used to denote an individual pod structure that includes at least one sensor responsive to (i.e., to detect) inputs from a user. Each of sensors 130 may be any type of sensor that is capable of detecting a signal produced, generated, or otherwise effected by and/or within the arm of the user, including but not limited to: an electromyography sensor, a magnetomyography sensor, a mechanomyography sensor, a microphone, a blood pressure sensor, a heart rate sensor, a gyroscope, an accelerometer, and/or a thermometer. In exemplary device 100, each of sensors 130 includes a respective electromyography ("EMG") sensor responsive to (i.e., to detect) input signals from the user in the form of electrical signals produced by muscle activity. Wearable electronic device 100 may transmit information based on the detected input signals to provide a human-electronics interface (e.g., a human-computer interface). Further details of exemplary electromyography device 100 are described in at least U.S. Non-Provisional patent application Ser. No. 14/186,889, U.S. Non-Provisional patent application Ser. No. 14/194,252, U.S. Provisional Patent Application Ser. No. 61/869,526 (now U.S. Non-Provisional patent application Ser. No. 14/465,194), U.S. Provisional Patent Application Ser. No. 61/909,786 (now U.S. Non-Provisional patent application Ser. No. 14/553,657), and U.S. Provisional Patent Application Ser. No. 61/915,338 (now U.S. Non-Provisional patent application Ser. No. 14/567,826), each of which is incorporated herein by reference in its entirety. Those of skill in the art will appreciate, however, that a wearable electronic device having electromyography functionality is used only as an example in the present systems, articles, and methods and that the systems, articles and methods for wearable electronic devices that employ elastic electrical cables to accommodate different user forms described herein are in no way limited to wearable electronic devices that employ electromyography sensors unless explicitly recited in a respective claim to such.

In general, the use of adaptive couplers in annular wearable electronic devices allows the circumference of the device (100) to vary (i.e., expand and contract) in at least one dimension (e.g., in magnitude) in order to accommodate (i.e., to fit) the form of the part of the user (e.g., forearm or leg) upon which the device is worn. This feature is very useful in implementing a "one size fits all" design for a wearable electronic device, and is further advantageous in wearable electronic devices employing sensors (e.g., 130) because the even/uniform expansion/contraction afforded by the adaptive couplers can maintain an approximately constant angular spacing between sensors located in different pod structures. Further details of adaptive coupling in wearable electronic devices employing sensors are described in, for example, U.S. Non-Provisional patent application Ser. No. 14/276,575, which is incorporated herein by reference in its entirety.

Pod structure 108 of device 100 includes a processor 140 that processes the signals provided by the EMG sensors 130 of sensor pods 101, 102, 103, 104, 105, 106, and 107 in response to detected muscle activity. Pod structure 108 may therefore be referred to as a "processor pod." Throughout this specification and the appended claims, the term "processor pod" is used to denote an individual pod structure that includes at least one processor to process signals. The processor may be any type of processor, including but not limited to: a digital microprocessor or microcontroller, an application-specific integrated circuit (ASIC), a field-programmable gate array (FPGA), a digital signal processor (DSP), a graphics processing unit (GPU), a programmable gate array (PGA), a programmable logic unit (PLU), or the like, that analyzes or otherwise processes the signals to determine at least one output, action, or function based on the signals. Implementations that employ a digital processor (e.g., a digital microprocessor or microcontroller, a DSP) may advantageously include a non-transitory processor-readable storage medium or memory 150 communicatively coupled thereto and storing processor-executable instructions that control the operations thereof, whereas implementations that employ an ASIC, FPGA, or analog processor may or may not include a non-transitory processor-readable storage medium 150.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 100, processor pod 108 includes an EMG sensor 130

(not visible in FIG. 1) responsive to (i.e., to sense, measure, transduce or otherwise detect) muscle activity of a user, so processor pod 108 could be referred to as a sensor pod. However, in exemplary device 100, processor pod 108 is the only pod structure that includes a processor 140, thus processor pod 108 is the only pod structure in exemplary device 100 that can be referred to as a processor pod. The processor 140 in processor pod 108 also processes the EMG signals provided by the EMG sensor 130 of processor pod 108. In alternative embodiments of device 100, multiple pod structures may include processors, and thus multiple pod structures may serve as processor pods. Similarly, some pod structures may not include sensors, and/or some sensors and/or processors may be laid out in other configurations that do not involve pod structures.

In device 100, processor 140 includes and/or is communicatively coupled to a non-transitory processor-readable storage medium or memory 150. Memory 150 may store processor-executable gesture identification instructions that, when executed by processor 140, cause processor 140 to process the EMG signals from EMG sensors 130 and identify a gesture to which the EMG signals correspond. For communicating with a separate electronic device (not shown), wearable electronic device 100 includes at least one communication terminal. Throughout this specification and the appended claims, the term "communication terminal" is generally used to refer to any physical structure that provides a telecommunications link through which a data signal may enter and/or leave a device. A communication terminal represents the end (or "terminus") of communicative signal transfer within a device and the beginning of communicative signal transfer to/from an external device (or external devices). As examples, device 100 includes a first communication terminal 161 and a second communication terminal 162. First communication terminal 161 includes a wireless transmitter (i.e., a wireless communication terminal) and second communication terminal 162 includes a tethered connector port 162. Wireless transmitter 161 may include, for example, a Bluetooth® transmitter (or similar) and connector port 162 may include a Universal Serial Bus port, a mini-Universal Serial Bus port, a micro-Universal Serial Bus port, a SMA port, a THUNDERBOLT® port, or the like. Either in addition to or instead of serving as a communication terminal, connector port 162 may provide an electrical terminal for charging one or more batteries 170 in device 100.

For some applications, device 100 may also include at least one inertial sensor 180 (e.g., an inertial measurement unit, or "IMU," that includes at least one accelerometer and/or at least one gyroscope) responsive to (i.e., to detect, sense, or measure) motion effected by a user and which provides signals in response to the detected motion. Signals provided by inertial sensor 180 may be combined or otherwise processed in conjunction with signals provided by EMG sensors 130.

Throughout this specification and the appended claims, the term "provide" and variants such as "provided" and "providing" are frequently used in the context of signals. For example, an EMG sensor is described as "providing at least one signal" and an inertial sensor is described as "providing at least one signal." Unless the specific context requires otherwise, the term "provide" is used in a most general sense to cover any form of providing a signal, including but not limited to: relaying a signal, outputting a signal, generating a signal, routing a signal, creating a signal, transducing a signal, and so on. For example, a surface EMG sensor may include at least one electrode that resistively or capacitively couples to electrical signals from muscle activity. This coupling induces a change in a charge or electrical potential of the at least one electrode which is then relayed through the sensor circuitry and output, or "provided," by the sensor. Thus, the surface EMG sensor may "provide" an electrical signal by relaying an electrical signal from a muscle (or muscles) to an output (or outputs). In contrast, an inertial sensor may include components (e.g., piezoelectric, piezoresistive, capacitive, etc.) that are used to convert physical motion into electrical signals. The inertial sensor may "provide" an electrical signal by detecting motion and generating an electrical signal in response to the motion.

As previously described, each of pod structures 101, 102, 103, 104, 105, 106, 107, and 108 may include electric circuitry (i.e., electrical and/or electronic circuitry). FIG. 1 depicts electric circuitry 121 inside the inner volume of sensor pod 101, electric circuitry 122 inside the inner volume of sensor pod 102, and electric circuitry 128 inside the inner volume of processor pod 118. The circuitry in any or all of pod structures 101, 102, 103, 104, 105, 106, 107 and 108 (including circuitries 111, 112, and 118) may include any or all of: an amplification circuit to amplify electrical signals provided by at least one EMG sensor 130, a filtering circuit to remove unwanted signal frequencies from the signals provided by at least one EMG sensor 130, and/or an analog-to-digital conversion circuit to convert analog signals into digital signals.

Signals that are provided by EMG sensors 130 in device 100 are routed to processor pod 108 for processing by processor 140. To this end, device 100 employs a set of communicative pathways (e.g., 191 and 192) to route the signals that are output by sensor pods 101, 102, 103, 104, 105, 106, and 107 to processor pod 108. Each respective pod structure 101, 102, 103, 104, 105, 106, 107, and 108 in device 100 is communicatively coupled to at least processor pod 108 of device 100. In some implementations, the signal(s) from any given sensor pod (e.g., 102) may be routed through one or more intervening sensor pod(s) (e.g., 101) en route to processor pod 108, whereas other implementations may employ a bus-like architecture in which the signal(s) from each sensor pod 101, 102, 103, 104, 105, 106 and 107 are routed directly to processor pod 108 without passing through intervening pod structures. In accordance with the present systems, articles, and methods, each communicative pathway (e.g., 191 and 192, only two illustrated and called out in FIG. 1 to reduce clutter) in device 100 is realized by a at least one flexible electrically conductive pathway that extends through the inner volume of adaptive coupler 111. For example, communicative pathway 191 comprises at least one flexible electrically conductive pathway that extends through a first portion of the inner volume of adaptive coupler 111 and electrically conductively couples to both electric circuitry 128 in processor pod 108 and electric circuitry 121 in sensor pod 101, and communicative pathway 192 comprises at least one electrically conductive pathway that extends through a second portion of the inner volume of adaptive coupler 111 and electrically conductively couples to both electric circuitry 128 in processor pod 108 (either directly, or through communicative pathway 191, or through one or more other communicative pathways) and electric circuitry 122 in sensor pod 102.

Device 100 from FIG. 1 represents an example of a wearable electronic device that employs an elastic electrical cable as an adaptive coupler in accordance with the present systems, articles, and methods. In device 100, an elastic electrical cable is used as adaptive coupler 111 to simultaneously provide both electrically conductive coupling and adaptive physical coupling between pod structures in the set of eight pod structures 101, 102, 103, 104, 105, 106, 107, and 108. Focusing in more detail on adaptive coupler 111, adaptive coupler 111 comprises an elastic electrical cable having at least one electrically conductive pathway (e.g., 191, 192) that is electrically conductively coupled to the respective electric circuitries of at least two pod structures in the set of pod structures 101, 102, 103, 104, 105, 106, 107, and 108, where at least a portion of the at least one electrically conductive pathway extends through (e.g., is contained within) an inner volume of an elastomer band 195. For example, adaptive coupler 111 includes electrically conductive pathway 192 that is electrically conductively coupled to the circuitry 121 of a first pod structure 101 and the circuitry 128 of a second pod structure 108. The at least one electrically conductive pathway 192 extends through (e.g., is contained within) an inner volume of an elastomer band 195, where the band 195 is also physically coupled to both the first pod structure 101 and the second pod structure 108. Since both the first pod structure 101 and the second pod structure 108 are positioned at least approximately on the circumference of device 100, the first pod structure 101 and the second pod structure 108 are physically separated from one another by a first distance at least approximately along the circumference of device 100. The portion of elastomer band 195 that couples in between first pod structure 101 and second pod structure 108 has a length that is greater than this first distance (i.e., greater than the distance along the circumference of device 100 that physically separates first pod structure 101 and second pod structure 108). This is because the length of elastomer band 195 that couples in between first pod structure 101 and second pod structure 108 includes at least one semi-rigidly set change in direction. The semi-rigidly set change in direction, for example, takes the form of a bend, turn, twist, curve, corner, step, or offset 199.

As previously described, an annular wearable electronic device (100) may employ multiple individual adaptive couplers each providing adaptive physical coupling between a respective set (e.g., between a respective pair) of pod structures, or an annular wearable device may employ one or more adaptive couplers that provide serial adaptive physical coupling between multiple sets (e.g., between multiple pairs) of pod structures. Device 100 employs two adaptive couplers 111 and 112 that each provide serial adaptive physical coupling between all pod structures 101, 102, 103, 104, 105, 106, 107, and 108 in device 100. Each of adaptive couplers 111 and 112 is positioned at least approximately on the circumference of device 100 and extends completely around the circumference of device 100. The elastic or resilient nature of adaptive couplers 111 and 112 ensures that, when not worn by a user, the circumference of annular wearable electronic device 100 is a relatively low value with adaptive couplers 111 and 112 each in a respective unstretched, relaxed, contracted, or default state. When worn by the user, the circumference of annular wearable electronic device 100 may be extended to encircle the portion of the user upon which device 100 is worn (e.g., the forearm) with adaptive couplers 111 and 112 each in a respective stretched or expanded state. The respective stretched or expanded state of each of adaptive couplers 111 and 112 is achieved by changing (i.e., reducing or increasing depending on the configuration) an angle of at least one of the semi-rigidly set changes in direction in the length of the corresponding band. For example, the stretched or expanded state of adaptive coupler 111 is achieved by reducing the angle (see FIG. 2) of the at least one semi-rigidly set change in direction 199 in at least one portion of band 195 that couples in between two adjacent ones of pod structures 101, 102, 103, 104, 105, 106, 107, and 108. In order to provide uniform expansion of device 100, adaptive coupler 111 may advantageously stretch or expand by reducing the angle of the at least one semi-rigidly set change in direction 199 in each portion of band 195 that couples in between two adjacent ones of pod structures 101, 102, 103, 104, 105, 106, 107, and 108.

Figure 2:
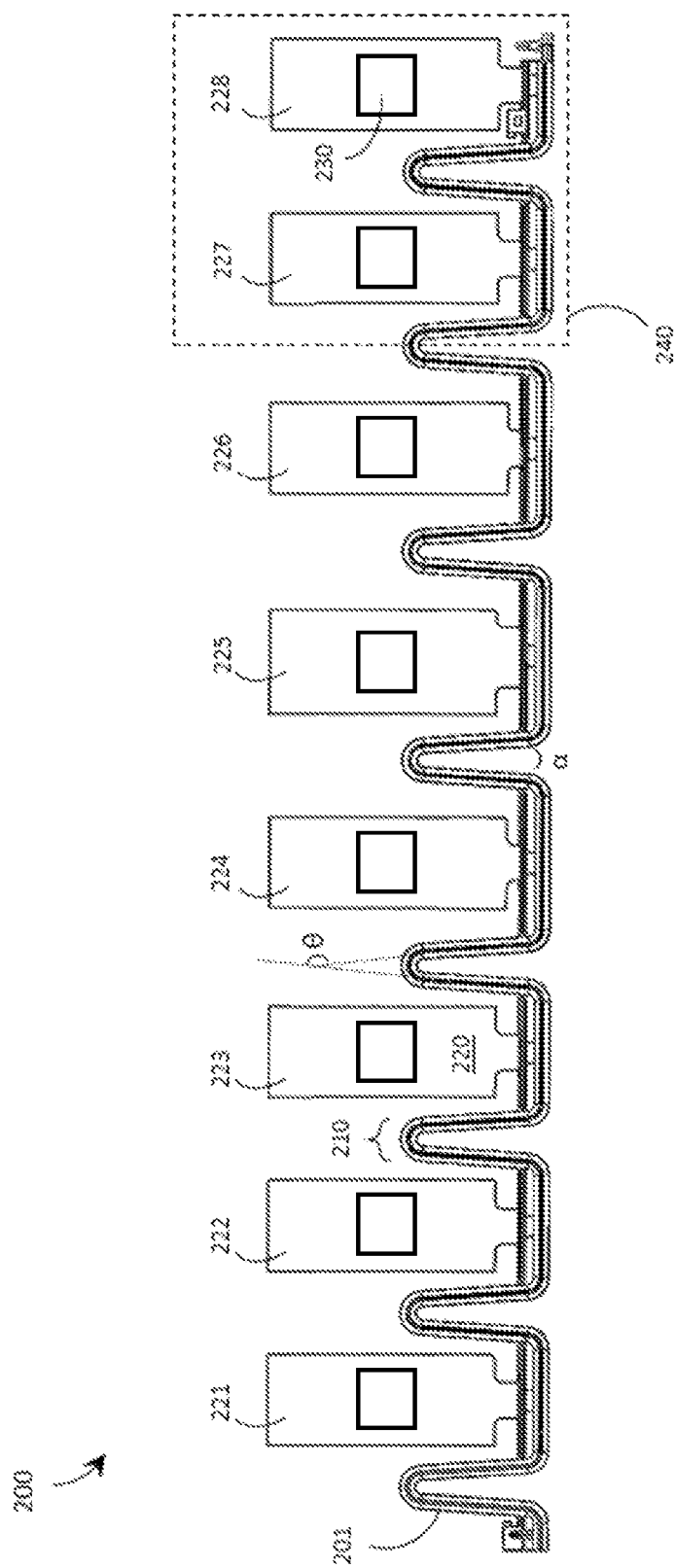
FIG. 2 is a plan view of an elastic electrical cable configured to be implemented as an adaptive coupler in an annular wearable electronic device in accordance with the present systems, articles, and methods.

In various embodiments of device 100, both of adaptive couplers 111 and 112 may include internal electrically conductive pathways (e.g., 191, 192) that electrically conductively couple to various ones of pod structures 101, 102, 103, 104, 105, 106, 107, and 108, or only one of adaptive couplers 111 and 112 may include internal electrically conductive pathways. In the embodiment of device 100 illustrated in FIG. 1, only adaptive coupler 111 includes internal electrically conductive pathways and provides electrically communicative coupling between various ones of pod structures 101, 102, 103, 104, 105, 106, 107, and 108 while adaptive coupler 112 provides only adaptive physical coupling between pod structures 101, 102, 103, 104, 105, 106, 107, and 108. Thus, adaptive coupler 111 is an elastic electrical cable while adaptive coupler 112 is, optionally, not. FIG. 2 provides more detail of an elastic electrical cable implemented as an adaptive coupler in a wearable electronic device, such as adaptive coupler 111 of device 100.

FIG. 2 is a plan view of an elastic electrical cable 200 configured to be implemented as an adaptive coupler in an annular wearable electronic device in accordance with the present systems, articles, and methods. For example, elastic electrical cable 200 may be used as adaptive coupler 111 in device 100 from FIG. 1. Cable 200 comprises a band 201 formed of a molded elastomer (i.e., an elastomer band, analogous to band 195 of adaptive coupler 111 from FIG. 1), where the length of the band 201 follows a tortuous path including a number of changes in direction that are semi-rigidly set into the molded elastomer. Throughout this specification and the appended claims, the term "set" as in "semi-rigidly set" is used to indicate that a feature is shaped, molded, or otherwise deliberately formed. The semi-rigid changes in direction may be set by the molding process by which elastomer band 201 is formed. Throughout this specification and the appended claims, the term "semi-rigid," and variants such as "semi-rigidly," are used to describe a shape or configuration of a material that allows limited deformation under moderate stresses and strains but exhibits a restoring force that effects an inherent resiliency, i.e., a tendency to return to its original shape or configuration when the stresses or strains are removed. For example, a sponge has a semi-rigid shape because it will deform when squeezed but will return to its original shape when the squeezing is stopped.

Throughout this specification and the appended claims, a "change in direction" is often described as being "semi-rigid" and/or "semi-rigidly set" into a length of an elastomer band. For the purposes of the present systems, articles, and methods, a "semi-rigid change in direction" (such as a semi-rigidly set change in direction) is a turn, twist, bend, step, curve, corner, or offset that has a fixed angle in the absence of stresses or strains or other applied forces, allows limited deformation of the angle (i.e., increases and/or decreases in the angle) in response to moderate applied stresses and strains, and has an inherent tendency to return back to the original angle when the applied stresses or strains are removed. The inherent tendency to return back to the original angle manifests itself as a restoring force that renders the elastomer band "elastic" or resilient. Semi-rigid changes in direction may be "set" into a path or length of a band material through the process by which the path or length of band material is formed and/or shaped. As an example, a "semi-rigid change in direction" may be "set" into a length of an elastomer band through a molding process by which the band is formed and shaped.

Band 201 of FIG. 2 includes a number (specifically, twenty-four in the illustrated example) of semi-rigidly set changes in direction 210 (only one called out in FIG. 2 to reduce clutter), each of which has a respective angle θ (only one called out in FIG. 2 to reduce clutter) that increases/decreases in size when, for example, the two portions of band 201 on either side of the location of the change in direction are pushed together or pulled apart. Because the changes in direction 210 in band 201 are semi-rigidly set, they render band 201 "elastic" or resilient by imparting restoring forces to the angles θ when the two portions of band 201 on either side of the location of each change in direction are pushed together or pulled apart. A person of skill in the art will appreciate that a change in direction may be characterized by an angle in different ways. An example angle θ is shown in FIG. 2 which characterizes a change in direction 210 from the point of view of one travelling along the path of band 201. By analogy, a car travelling along band 201 would have to rotate itself by θ in order to accomplish the corresponding change in direction 210. With θ defined this way, the angle of the change in direction 210 will decrease when two portions of band 201 on either side of the change in direction 210 are pulled apart (i.e., band 201 is stretched) and increase when those same two portions of band 201 are pushed together (i.e., band 201 is compressed). But a person of skill in the art will appreciate that this definition of θ is arbitrary. For example, a perfectly viable alternative would be to characterize the angle of each change in direction by the angle formed in between the two portions of the band 201 on either side of the change in direction 210, shown as angle α in FIG. 2. Since α=180°−θ, the angle of the change in direction 210 will increase when two portions of band 201 on either side of the change in direction 210 are pulled apart (i.e., band 201 is stretched) and decrease when those same two portions of band 201 are pushed together (i.e., band 201 is compressed) if the angle is defined as a instead of θ.

The number of changes in direction along the length of band 201 characterize a tortuous path. Throughout this specification and the appended claims, the expression "tortuous path" is used to generally describe a length that connects between two points and includes a number of changes in direction instead of a direct or straight line. As examples, a tortuous path may be described as meandering, winding, circuitous, or convoluted and may include changes in direction that result in a serpentine, crenulated, crenelated, boustrophedonic, "zig-zag," or "back-and-forth" pattern. Such changes in direction may include corners or sharp angles (e.g., right-angles), curves, bends, steps, twists, turns, coils, offsets, or any combination thereof. In the illustrated example of cable 200 in FIG. 2, such changes in direction are planar (i.e., in the same plane) such that the entire length of cable 200 lies, at least approximately and while cable 200 is not bent into, for example, an annular configuration to serve as an adaptive coupler in an annular wearable electronic device, in a single plane.

Though not visible in the plan view of FIG. 2, the length of band 201 includes an inner volume that is devoid of elastomer material. As described in more detail later on, this inner volume may be established through the process by which band 201 is formed and/or shaped, such as through a molding process. In accordance with the present systems, articles, and methods, at least a portion of the inner volume of band 201 contains at least a portion of at least one flexible electrically conductive pathway. The at least one flexible electrically conductive pathway may comprise an electrically conductive trace carried on a flexible substrate. For example, the at least one electrically conductive pathway may be part of a flexible printed circuit board 220.

Exemplary elastic electrical cable 200 is specifically configured for use as adaptive coupler 111 in annular wearable electronic device 100 of FIG. 1. As such, the flexible printed circuit board 220 that extends through the inner volume of band 201 includes several portions or ends 221, 222, 223, 224, 225, 226, 227, and 228 that extend or protrude out of the inner volume of band 201 at various locations. Each of the eight portions or ends 221, 222, 223, 224, 225, 226, 227, and 228 of flexible printed circuit board 220 that extends out of the inner volume of band 201 corresponds to a respective pod structure 101, 102, 103, 104, 105, 106, 107, and 108 of device 100 and provides electrically conductive coupling to the electric circuitry (e.g., 121, 122, 128) therein. In the illustrated example of cable 200, each of the eight portions or ends 221, 222, 223, 224, 225, 226, 227, and 228 of flexible printed circuit board 220 that extends out of the inner volume of band 201 includes, either carried directly on flexible printed circuit board 220 or carried on a rigid printed circuit board that is coupled to flexible printed circuit board 220, at least a portion of the electric circuitry (generally represented by circuit component 230, with only one called out in FIG. 2 to reduce clutter) of a corresponding pod structure 101, 102, 103, 104, 105, 106, 107, and 108 of device 100. However, in alternative applications, an elastic electrical cable may, in accordance with the present systems, articles, and methods, include any number of portions or ends of flexible electrically conductive pathways that extend out of the inner volume of the band for the purpose of providing electrically conductive couplings to devices or components of devices.

Each of the eight portions or ends 221, 222, 223, 224, 225, 226, 227, and 228 of flexible printed circuit board 220 that extends out of the inner volume of band 201 does so at an at least approximately right-angle to the length of cable 200. This feature (among other features) renders cable 200 particularly well-suited for use in applications (such as circumferential adaptive coupler 111 in annular wearable electronic device 100) where stretching forces are expected along the length of cable 200. Because the eight portions or ends 221, 222, 223, 224, 225, 226, 227, and 228 of flexible printed circuit board 220 extend substantially perpendicularly out from band 201 (relative to the length of band 201; i.e., in a transverse direction), electrical connections made to the eight portions or ends 221, 222, 223, 224, 225, 226, 227, and 228 of flexible printed circuit board 220 are not directly subjected to longitudinal stretching forces along the length of band 201.

Figure 3A:
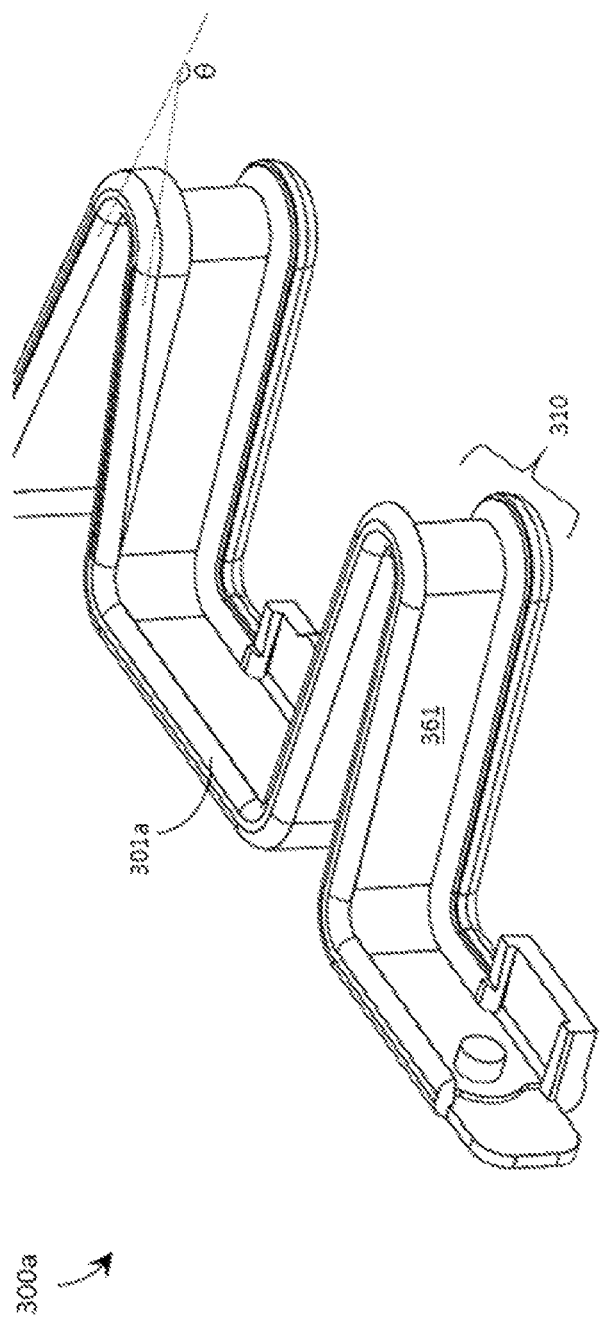
FIG. 3A is a perspective view of a portion of an elastic electrical cable after the first stage of a multi-stage (or "multi-shot") overmolding fabrication process in accordance with the present systems, articles, and methods.
Figure 3B:
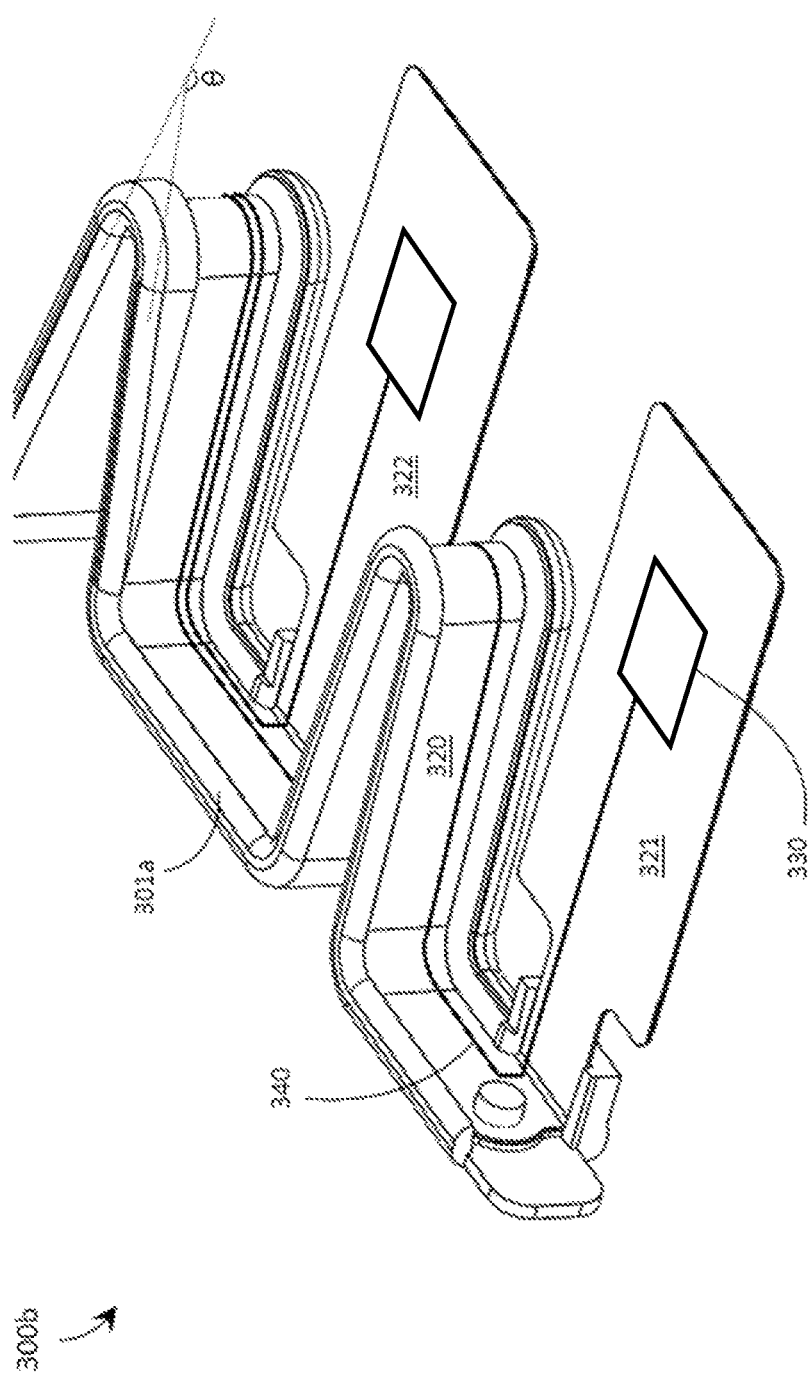
FIG. 3B is a perspective view of a portion of an elastic electrical cable after a second stage of a multi-stage (or "multi-shot") overmolding fabrication process in accordance with the present systems, articles, and methods.
Figure 3C:
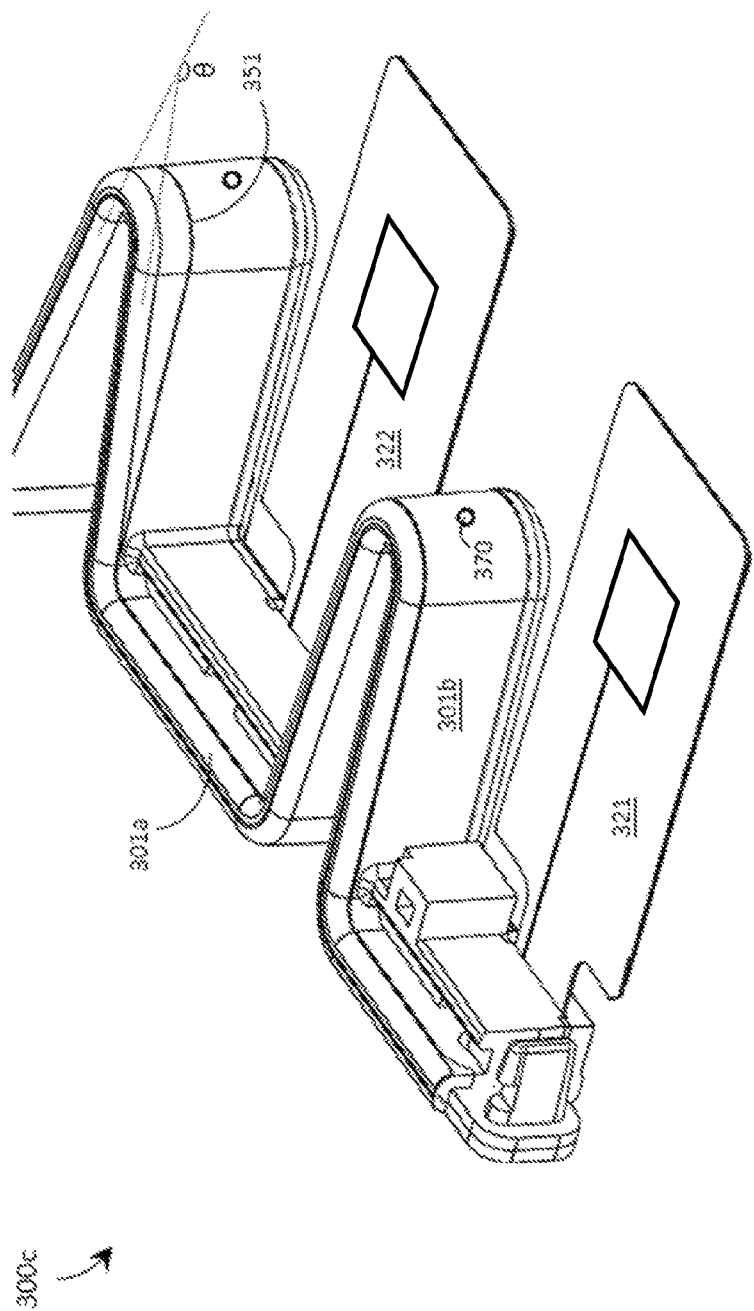
FIG. 3C is a perspective view of a portion of an elastic electrical cable after a third stage of a multi-stage (or "multi-shot") overmolding fabrication process in accordance with the present systems, articles, and methods.

As previously described, cable 200 (and particularly, elastomer band 201 of cable 200) may be formed and shaped by a molding process. In accordance with the present systems, articles, and methods, elastic electrical cables (such as cable 200) may be formed by a multi-stage (or "multi-shot") overmolding process in which: i) a first longitudinal section or portion of the elastomer band 201 is molded by a first molding stage or "shot," the first longitudinal section having a recessed surface; ii) at least one flexible electrically conductive pathway (e.g., flexible printed circuit board 220) is deposited against the recessed surface of the first longitudinal section or portion; and iii) a second longitudinal section or portion of the elastomer band 201 is overmolded by a second molding stage or "shot" to define an "overmold portion" over the flexible electrically conductive pathway and at least a portion of the first longitudinal section of the elastomer band 201. This process produces an elastic elastomer cable (e.g., 200) having two longitudinal or "lengthwise" portions, segments, or sections of elastomer band (e.g., 201) that, together, enclose an inner volume through which at least one electrically conductive pathway extends. FIGS. 3A, 3B, and 3C each provides an illustrative example of cable 200 from FIG. 2 at a respective one of these three fabrication stages.

FIG. 3A is a perspective view of a portion 300a of an elastic electrical cable (e.g., cable 200 from FIG. 2) after the first stage of a multi-stage (or "multi-shot") overmolding fabrication process in accordance with the present systems, articles, and methods. Portion 300a comprises a first longitudinal section 301a of an elastomer band molded to include a recessed surface 361 and a number of semi-rigid (i.e., semi-rigidly set) changes in direction 310 (only one called out in FIG. 3A to reduce clutter). Each semi-rigid change in direction is characterized by a respective angle θ (again, only one called out in FIG. 3A to reduce clutter, and the choice of the definition of angle θ is arbitrary; i.e., an angle α=180°−θ could similarly be used to characterize change in direction 310) which may change in magnitude when first longitudinal section 301a is subjected to stresses and strains (e.g., when the ends of first longitudinal section 301a are pushed together or pulled apart) but which intrinsically maintains/returns to substantially the same magnitude (i.e., the illustrated magnitude) when such stresses and strains are absent/removed. As discussed in more detail later on, first longitudinal section 301a may be formed of an elastomer material (such as any of a variety of thermoplastic elastomers available from Dupont) and formed using a first mold (i.e., a first molding tool).

FIG. 3B is a perspective view of a portion 300b of an elastic electrical cable (e.g., cable 200 from FIG. 2) after a second stage of a multi-stage (or "multi-shot") overmolding fabrication process in accordance with the present systems, articles, and methods. Portion 300b comprises the first longitudinal section 301a of an elastomer band from FIG. 3A and a flexible printed circuit board 320 deposited onto/against the recessed surface (361 from FIG. 3A, not visible in FIG. 3B due to the placement of flexible printed circuit board 320 thereon) of first longitudinal section 301a. Flexible printed circuit board 320 may be adhered to recessed surface 361 using an adhesive, such as a pressure sensitive adhesive. As described for cable 200 of FIG. 2, flexible printed circuit board 320 includes a number of portions 321, 322 that protrude out from and at substantially right angles to first longitudinal section 301a. Each such portion 321, 322 carries and/or electrically couples to electric circuitry (including discrete electrical components such as 330; only one called out in FIG. 3B to reduce clutter) which may be encapsulated in a pod structure (e.g., pod structures 101, 102, 103, 104, 105, 106, 107, and/or 108) of a wearable electronic device (e.g., device 100). Flexible printed circuit board 320 may carry any number of electrically conductive traces 340 which may route to/from or by-pass any or all of portions 321, 322 depending on the specific implementation.

FIG. 3C is a perspective view of a portion 300c of an elastic electrical cable (e.g., cable 200 from FIG. 2) after a third stage of a multi-stage (or "multi-shot") overmolding fabrication process in accordance with the present systems, articles, and methods. Portion 300c comprises the first longitudinal section 301a of elastomer from FIG. 3A with the flexible printed circuit board (320 from FIG. 3B, not visible in FIG. 3C) deposited onto/against the recessed surface (361 from FIG. 3A, not visible in FIG. 3C) of first longitudinal section 01a, and portion 300c further comprises a second longitudinal section 301b of elastomer overmolded over at least a portion of the flexible printed circuit board (320) and the recessed surface (361) of first longitudinal section 301a to enclose the at least a portion of the flexible printed circuit board (320) within an inner volume of elastomer. Portions 321, 322 of the flexible printed circuit board (320) protrude from the inner volume of elastomer and may subsequently be encapsulated by pod structures (e.g., 101, 102, 103, 104, 105, 106, 107, and/or 108) of a wearable electronic device (e.g., 100). Thus, second longitudinal section 301b of elastomer is molded to include the same semi-rigid (i.e., semi-rigidly set) changes in direction 310 (only one called out in FIG. 3C to reduce clutter) as first longitudinal section 301a, with each change in direction 310 characterized by a respective angle θ (only one called out FIG. 3C to reduce clutter) as for first longitudinal section 301a.

The perspective view of FIG. 3C shows that portion 300c comprises a first longitudinal section 301a and a second longitudinal section 301b (i.e., two longitudinally-divided halves), each of which spans the entire length of portion 300c (and, in general, the entire length of the elastic electrical cable, such as cable 200), and which are mated together to form longitudinal seams 351, 352. As will be discussed in more detail later, FIG. 3C also shows impressions 370 (only one called out in FIG. 3C to reduce clutter) corresponding to the deliberate locations of gates through which elastomer material is injected into the mold when the second longitudinal section 301b of the cable is formed.

With reference to each of FIGS. 3A, 3B, and 3C, the first longitudinal section 301a of molded elastomer has a recessed surface 361 that is sized and dimensioned to receive flexible printed circuit board 320. The depth of the recessed surface 361 may (as illustrated in FIGS. 3A, 3B, and 3C) be larger than the thickness of flexible printed circuit board 320 and second longitudinal section 301b of elastomer may be molded substantially into the recess to overmold flexible printed circuit board 320 and recessed surface 361 and substantially fill the depth of the recess. Alternatively, the depth of the recessed surface 361 may be at least approximately equal to the thickness of flexible printed circuit board 320.

With the flexible printed circuit board 320 deposited on, affixed to, adhered to, or otherwise placed against or carried by the recessed surface 361 of the first molded longitudinal section 301a of elastomer, the second "overmold" longitudinal section 301b of elastomer is overmolded over at least a portion of the exposed surface of flexible printed circuit board 320 and over at least a portion of the first molded longitudinal section 301a. In this way, at least a portion of flexible printed circuit board 320 is enclosed or contained within an inner volume of elastomer, the inner volume being defined by a space in between first longitudinal section 301a and second longitudinal section 301b. However, the resulting cable (e.g., 200) may further include holes or access points out of which portions or ends (e.g., 321, 322) of flexible printed circuit board 320 (or one or more connector(s) coupled thereto) may protrude or be accessible (e.g., ports) in order to provide electrically conductive couplings to other devices or components of devices (e.g., to pod structures in annular wearable electronic device 100). In some applications, the process of curing the second "overmold" portion having a hole out of which a portion of an electrically conductive pathway protrudes may shrink the overmold elastomer and result in a tight, substantially hermetic seal around the protruding portion of the electrically conductive pathway.

The use of the elastic electrical cables described herein (e.g., cable 200 from FIG. 2) as adaptive couplers in wearable electronic devices (e.g., as adaptive coupler 111 in annular wearable electronic device 100 from FIG. 1) is an example application for which the cables are particularly well-suited. The cables are particularly well-suited for this application because in use they may simultaneously provide both electrically conductive coupling and adaptive physical coupling between otherwise physically and electrically separate parts. In a wearable electronic device, such electrically conductive coupling is necessary for the device to function electrically and such adaptive physical coupling enables the device to expand and contract in order to accommodate the movements of a user and/or different user forms. However, as described in the context of FIGS. 4A and 4B below, the elastic electrical cables described herein may be generalized for use in any system where electrically conductive coupling, adaptive physical coupling, or both are desired.

Figure 4A:
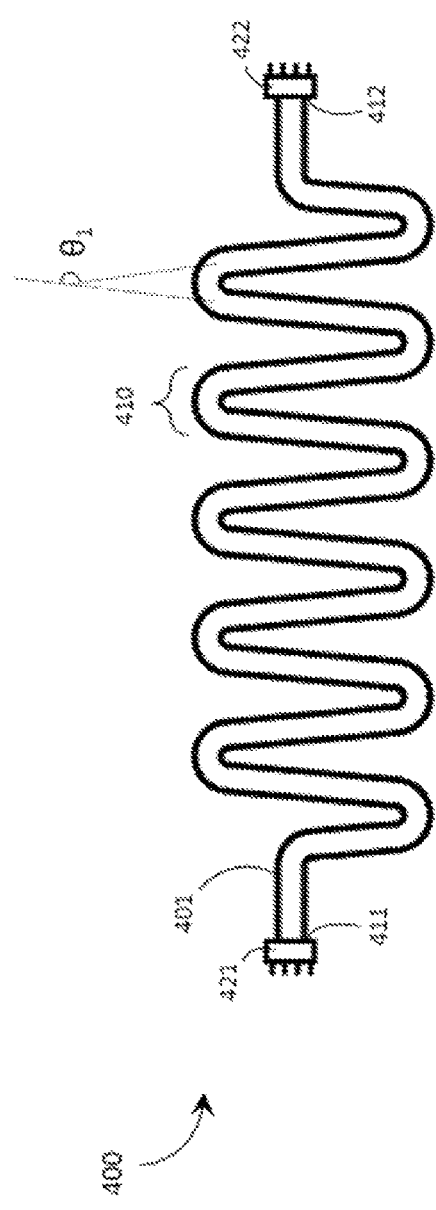
FIG. 4A is a plan view of an elastic electrical cable in an unstretched state in accordance with the present systems, articles, and methods.

FIG. 4A is a plan view of an elastic electrical cable 400 in an unstretched, contracted, or relaxed state in accordance with the present systems, articles, and methods. Similar to cable 200 from FIG. 2, cable 400 comprises an elastomer band 401 through which at least one flexible electrically conductive pathway (e.g., in the form of a conductive trace carried on or by a flexible printed circuit board) extends (i.e., in an inner volume thereof). Elastomer band 401 is formed by a multi-stage molding process in which a first longitudinal section of band 401 is molded, the at least one flexible electrically conductive pathway is deposited thereon/therein, and a second "overmold" longitudinal section of band 401 is overmolded over at least a portion of the at least one flexible electrically conductive pathway and over at least a portion of the first longitudinal section of band 401 in order to enclose at least a portion of the at least one flexible electrically conductive pathway within band 401. This process produces at least one longitudinal mating seam (not visible in the plan view of cable 400 in FIG. 4A). A first end of the at least one flexible electrically conductive pathway (not visible in FIG. 4A) is proximate (e.g., extends out of) a first end 411 of band 401 where it is electrically conductively coupled to a first electrical connector 421, while a second end of the at least one electrically conductive pathway (also not visible in FIG. 4A) is proximate (e.g., extends out of) a second end 412 of band 401 where it is electrically conductively coupled to a second electrical connector 422. First electrical connector 421 and second electrical connector 422 are both depicted as male, pin-type connectors in the example of cable 400; however, a person of skill in the art will appreciate that any type of electrical connector, including male and female electrical connectors, may be substituted for first electrical connector 421 and/or for second electrical connector 422 depending on the specific application of cable 400.

Similar to cable 200 from FIG. 2, cable 400 includes a number of semi-rigidly set changes in direction 410 (only one called out in FIG. 4A to reduce clutter) that characterize a tortuous path along the length of cable 400. The number of changes in direction 410 may be semi-rigidly set into the length of cable 400 by the molding process through which cable 400 is formed and shaped. For example, when a multi-stage molding process is used as described above, the number of changes in direction 410 may be first semi-rigidly set into the first longitudinal section of band 401 during the first stage or "shot" of the multi-stage molding process and then similarly semi-rigidly set into the second longitudinal section of band 401 during the second stage or "shot" (i.e., the overmolding stage) of the multi-stage molding process.

While cable 400 is in an unstretched or relaxed state, each semi-rigidly set change in direction 410 is characterized by a first angle $\theta_1$ (only one called out in FIG. 4A to reduce clutter). In other words, each change in direction 410 in cable 400 is semi-rigidly set (e.g., by a molding process) to embody a respective first angle $\theta_1$. Respective first angles $\theta_1$, may or may not be substantially equal for any or all respective ones of changes in direction 410. The "semi-rigidly set" nature of each first angle $\theta_1$ means that each change in direction 410 in cable 400 exhibits an inherent restoring force that strives to return the respective angle of each change in direction 410 back to its corresponding first angle $\theta_1$ if and when the angle is changed (due to, for example, an expansion, twist, or contraction of cable 400).

FIG. 4A depicts cable 400 in an unstretched, contracted, or relaxed state in which the angle of each change in direction 410 is its corresponding first angle $\theta_1$. For comparison, FIG. 4B shows the same cable 400 in a stretched or expanded state in which the angle of each change in direction 410 is a respective second angle $\theta_2$.

Figure 4B:
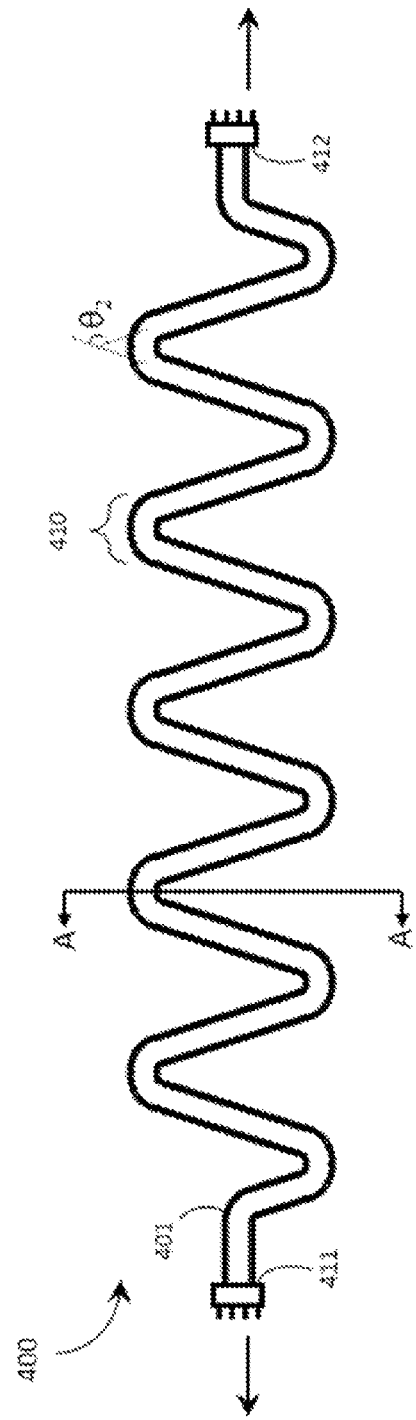
FIG. 4B is a plan view of the elastic electrical cable from FIG. 4A in a stretched state in accordance with the present systems, articles, and methods.

FIG. 4B is a plan view of elastic electrical cable 400 from FIG. 4A in a stretched, expanded, or tense state in accordance with the present systems, articles, and methods. Stretching of cable 400 may be accomplished by, for example, pulling first end 411 and/or second end 412 further apart from one another in the directions indicated by the arrows in FIG. 4B. Such may, for example, result from an increase in a diameter or radius (or an increase in the magnitude of the circumference) of an annular or closed loop structure of which the cable 400 is a part. In the stretched state, each semi-rigidly set change in direction 410 in cable 400 is characterized by a respective second angle $\theta_2$ (only one called out in FIG. 4B to reduce clutter) that is different from its corresponding first angle $\theta_1$. With the angles $\theta$ defined as they are in FIGS. 4A and 4B, stretching cable 400 reduces the magnitude of the respective angle of each change in direction 410 so that $\theta_2 < \theta_1$. However, as previously described the angle that characterizes a change in direction 410 may also be characterized in such a way (e.g., as $\alpha = 180° - \theta$) that stretching the cable may result in increases in one or more angle(s). In accordance with the present systems, articles, and methods, what is common to all implementations of the elastic electrical cables described herein is that stretching the cable causes the angle(s) of one or more semi-rigidly set change(s) in direction to change and gives rise to one or more restoration force(s) that strive(s) to return the one or more angle(s) to the original value(s). The restoration force(s) is/are the source of the elasticity or resiliency of the elastic electrical cables described herein.

FIG. 4B depicts a simple stretched or expanded state of cable 400 in which the cable is essentially elongated along its longitudinal axis. In other words, FIG. 4B shows only a one-dimensional stretch across a single degree of freedom. A person of skill in the art will appreciate that the elastic electrical cables described herein may accommodate stretches or compressions (i.e., extensions or contractions) in all three spatial dimensions (i.e., first end 411 and second end 412 of cable 400 may be repositioned relative to one another in any or all of the three spatial dimensions) and, furthermore, the elastic electrical cables described herein may accommodate torsions, twists, curls, bends, and other stresses/strains across a wide range of degrees of freedom.

As previously described, cable 400 comprises an elastomer band 401 that includes an inner volume through which at least a portion of at least one flexible electrically conductive pathway (e.g., at least one flexible printed circuit board) at least partially extends. A sectional view of cable 400 is provided in order to illustrate this inner volume.

Figure 4C:
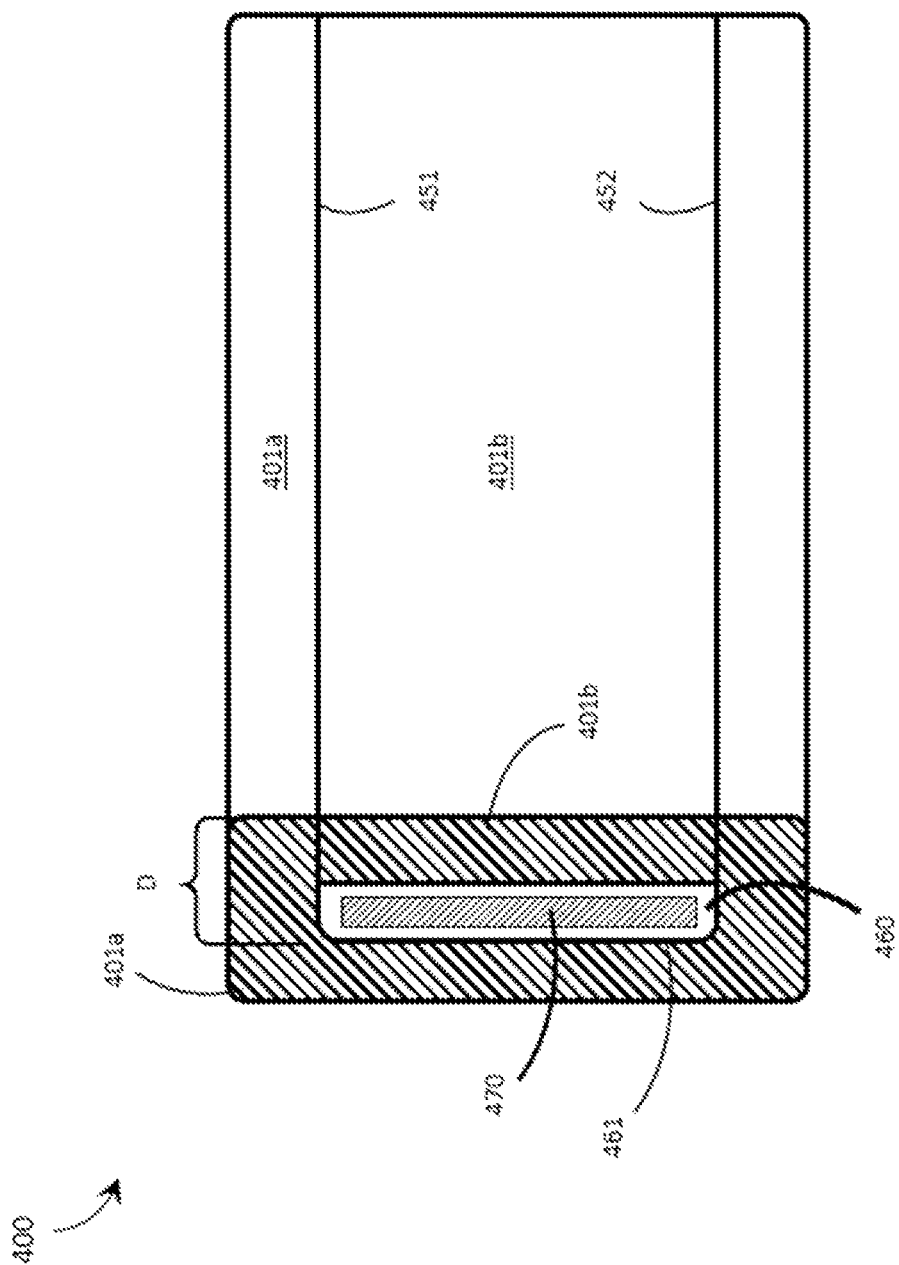
FIG. 4C is a sectional view of the elastic electrical cable along the line A-A from FIG. 4B.

FIG. 4C is a sectional view of elastic electrical cable 400 along the line A-A from FIG. 4B. In the sectional view of FIG. 4C, it is clearly seen that elastomer band 401 comprises a first longitudinal section (or "length") 401a and a second longitudinal section (or "length") 401b with an inner volume 460 enclosed therebetween. Furthermore, the sectional view of FIG. 4C also shows flexible printed circuit board 470 contained within inner volume 460 of band 401. The size of inner volume 460 (specifically, relative to the size of flexible printed circuit board 470) is exaggerated in FIG. 4C to enhance visual clarity. In practice, inner volume 460 may have substantially the same cross sectional area as flexible printed circuit board 470 so that there are little to no gaps present in inner volume 460 when flexible printed circuit board 470 is contained therein. The first and second longitudinal sections 401a, 401b, respectively, of band 401 are mated together along longitudinal mating seams 451, 452. Seams 451 and 452 are depicted on the same side/surface of band 401 in FIG. 4C and on a side/surface of band 401 that is widest. In some applications, this placement of seams 451 and 452 may advantageously mitigate splitting along the seams (e.g., in comparison to a configuration in which seams 451 and 452 are located on symmetrically aligned points on two opposing surfaces of band 401); however, in other applications either or both of seams 451 and/or 452 may be architected to form elsewhere on band 401 (e.g., on a different side/surface of band 401).

In the illustrated example of FIG. 4C, the inner volume 460 of cable 400 is completely defined within the first longitudinal section 401a of elastomer. As previously described, the first longitudinal section of an elastomer band may be molded, in accordance with the present systems, articles, and methods, to include a recessed surface that is sized and dimensioned to receive a flexible printed circuit board. In cable 400, recessed surface 461 is molded into first longitudinal section 401a of elastomer to receive flexible printed circuit board 470. A layer of adhesive, such as pressure sensitive adhesive (not shown in FIG. 4C) may be applied to either flexible printed circuit board 470 or recessed surface 461, or both, to adhere flexible printed circuit board 470 to recessed surface 461. Once first longitudinal section 401a is molded and flexible printed circuit board 470 is deposited in place on or against recessed surface 461, second longitudinal section 401b is overmolded over both flexible printed circuit board 470 and first longitudinal section 401a (e.g., over recessed surface 461 of first longitudinal section 401a) in order to define inner volume 460 in which flexible printed circuit board 470 is contained. As previously described, the depth D of recessed surface 461 may be greater than the thickness of flexible printed circuit board 470 so that second longitudinal section 401b of elastomer fills the remaining depth (i.e., over flexible printed circuit board 470) of the recess during the overmolding process.

The various embodiments of elastic electrical cables described herein, including the generic cable implementations of FIGS. 4A, 4B, and 4C and the adaptive coupler implementations of FIGS. 1, 2, 3A, 3B, and 3C, all commonly describe cables that are prepared, fabricated, formed, and/or shaped by a particular process or method. This method is summarized in FIG. 5.

Figure 5:
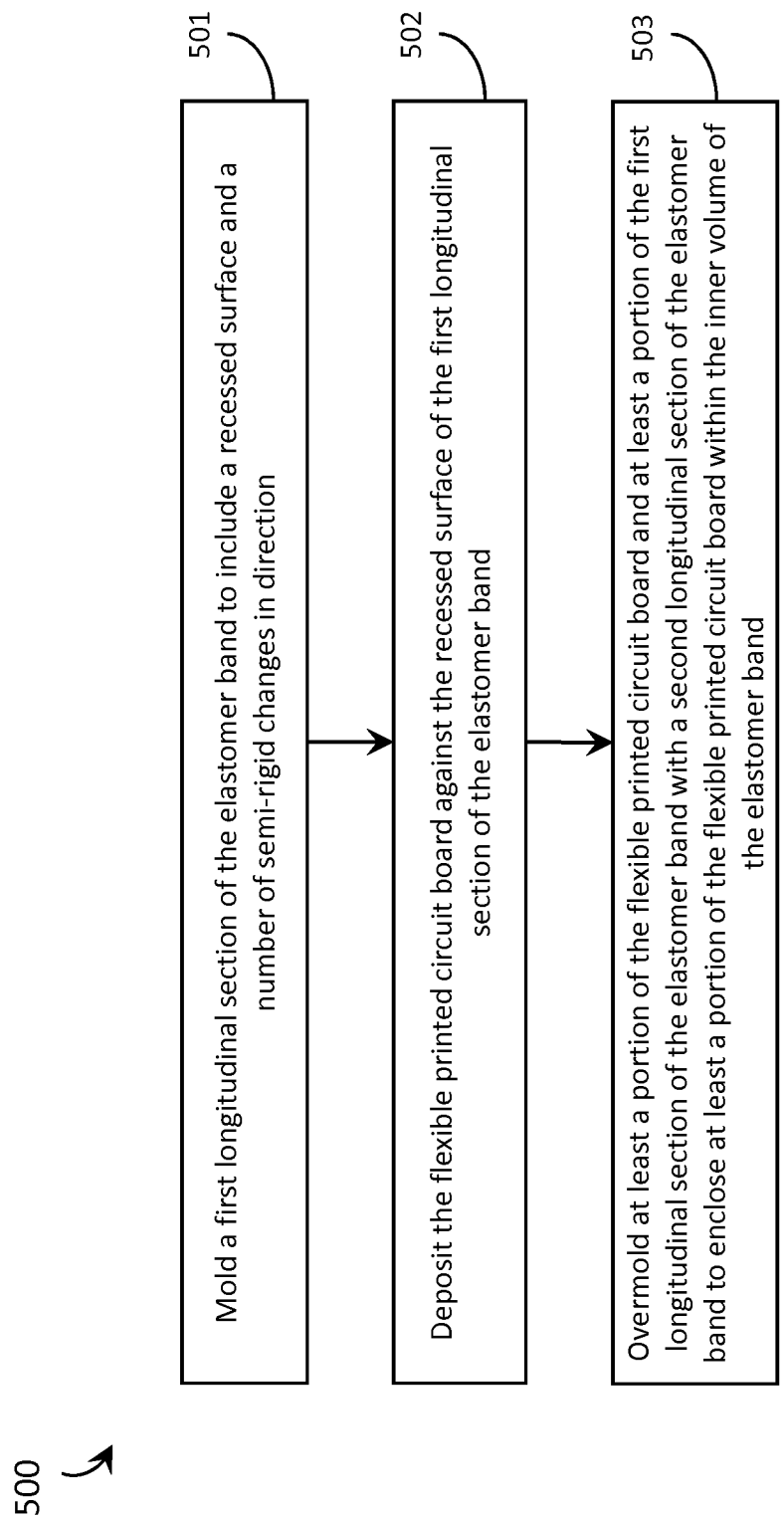
FIG. 5 is a flow-diagram showing a method of fabricating an elastic electrical cable in accordance with the present systems, articles, and methods.

FIG. 5 is a flow-diagram showing a method 500 of fabricating an elastic electrical cable in accordance with the present systems, articles, and methods. The elastic electrical cable comprises a flexible printed circuit board that at least partially extends through an inner volume of an elastomer band as illustrated in the examples of adaptive coupler 111 (FIG. 1), cable 200 (FIG. 2), portion 300c (FIG. 3C), and cable 400 (FIGS. 4A, 4B, and 4C). Method 500 includes three acts 501, 502, and 503, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. To exemplify the relationship between the acts of method 500 and the elements of the elastic electrical cables described herein, reference to elements of cable 400 from FIGS. 4A, 4B, and 4C are included in parentheses throughout the description of method 500. However, a person of skill in the art will appreciate that method 500 similarly applies to the fabrication of cable 200 from FIG. 2, to adaptive coupler 111 from FIG. 1, to portion 300c from FIG. 3C, and generally to any elastic electrical cable incorporating the teachings of the present systems, articles, and methods.

At 501, a first longitudinal section (401a) of the elastomer band (401) component of the elastic electrical cable (400) is molded. The first longitudinal section (401a) includes a recessed surface (461) and a number of semi-rigidly set changes in direction (410). In other words, molding the first longitudinal section (401a) of the elastomer band (401) includes molding a recessed surface (461) into the first longitudinal section (401a) and setting a number of semi-rigid changes in direction (410) along the first longitudinal section (401a).

At 502, the flexible printed circuit board (470) component of the elastic electrical cable (400) is deposited onto or against the recessed surface (461) of the first longitudinal section (401a) of the elastomer band (401). Depositing the flexible printed circuit board (470) onto or against the recessed surface (461) may include bending the flexible printed circuit board (470), by hand or using a mechanical apparatus or jig, to match the number of changes in direction (410) along the first longitudinal section (401a) of the elastomer band (401) and positioning the bent flexible printed circuit board (470) against the recessed surface (461) of the first longitudinal section (401a) of the elastomer band (401). In some implementations, a layer of pressure sensitive adhesive may be deposited on or otherwise applied to either a first surface of the flexible printed circuit board (470), or to the recessed surface of the first longitudinal section (401a) of elastomer, or to both, and depositing the flexible printed circuit board (470) onto or against the recessed surface (461) of the first longitudinal section (401a) of the elastomer band (401) may include pressing the flexible printed circuit board (470) against the recessed surface (461) of the first longitudinal section (401a) of the elastomer band (401) to activate the pressure sensitive adhesive and adhere the first surface of the flexible printed circuit board (470) to the recessed surface (461) of the first longitudinal section (401a) of the elastomer band (401). A person of skill in the art will appreciate that in alternative implementations, either no adhesive or a different form of adhesive may be used, such as a temperature sensitive adhesive or a UV light sensitive adhesive if, for example, the elastomer material used to form the first longitudinal section (401a) is transparent to UV light. Likewise, in some implementations one or more mechanical molded feature(s) (e.g., tongue and groove, chamfered or beveled edges, tabs, protrusions, and the like) may be included in the first and/or the second longitudinal section(s) to hold the flexible printed circuit board (470) in place.

At 503, the flexible printed circuit board (470) (i.e., the exposed surface thereof which is opposite the surface that is positioned against the recessed surface (461) of the first longitudinal section (401*a*) of the elastomer band (401)) and at least a portion of the first longitudinal section (401*a*) of the elastomer band (401) are overmolded with a second longitudinal section (401*b*) of the elastomer band (401). Overmolding the flexible printed circuit board (470) and at least a portion of the first longitudinal section (401*a*) of the elastomer band (401) with a second longitudinal section (401*b*) of the elastomer band (401) encloses at least a portion of the flexible printed circuit board (470) within the inner volume (460) of the elastomer band (401) and may result in one or more longitudinal mating seam(s) (451, 452) between the first longitudinal section (401*a*) and the second longitudinal section (401*b*) of the elastomer band (401).

In a typical overmolding process, multiple molding steps or "shots" may be carried out using the same mold. In other words, a first portion of a structure is typically molded using (e.g., by injection of a moldable material into) a first portion of a mold and then a second portion of the structure is molded over at least a portion of the first portion of the structure using (e.g., by injection of a moldable material into) a second portion of the mold. However, in method 500, it can be advantageous to use two separate molds (i.e., a first mold for the first longitudinal section of elastomer and a second mold for the second longitudinal section of elastomer). In this way, the first longitudinal section of elastomer may be removed from the first mold and the flexible printed circuit board may be deposited onto/against the recessed surface of the first longitudinal section of elastomer while the first longitudinal section of elastomer is outside of the first mold. In some implementations, the first longitudinal section of elastomer may be deposited onto an inner surface of the second mold and the flexible printed circuit board may be deposited onto/against the recessed surface of the first longitudinal section of elastomer while the first longitudinal section of elastomer is on the inner surface of the second mold. This configuration allows the flexible printed circuit board to be pressed against the recessed surface of the first longitudinal section of elastomer (either by hand or by a mechanical apparatus such as a jig) and secured in place while the first longitudinal section of elastomer is in the second mold. If a pressure sensitive adhesive layer is used in between the recessed surface of the first longitudinal section of elastomer and the flexible printed circuit board, then this configuration also allows the pressure sensitive adhesive layer to be activated within the second mold.

In a typical molding process (whether involving overmolding or not), a mold is designed to be some percentage larger than the actual intended size of the structure being molded. This is to accommodate for shrinkage of the molded structure during cooling/curing of the molded material. For example, molded elastomer structures typically shrink during the cooling/curing stage of the molding process and the corresponding mold is typically dimensioned to accommodate for this X % shrinkage (i.e., sized a corresponding percentage larger than the intended final size of the molded structure).

Shrinkage effects are particularly influential in overmolding processes such as those described in the present systems, articles, and methods. Unanticipated shrinkage of an overmolding layer (i.e., of a molded layer that overmolds one or more other layer(s)) can compromise the entire molded structure by, for example, producing unintended warping, pinching, crimping, or other such effects. The present systems, articles, and methods teach ways in which unwanted shrinkage effects in an elastic electrical cable in which one or more elastomer layers overmold a flexible printed circuit board can be mitigated.

Using two separate molds, the first mold may be sized and dimensioned to accommodate 0% shrinkage of the first longitudinal section of the elastomer band. In other words, the first mold may not incorporate any adjustment or tolerance to account for shrinkage of the first longitudinal section of elastomer so that after cooling/curing the first longitudinal section of elastomer shrinks to a size that is in fact smaller than the intended final size of the elastomer band. Throughout this specification and the appended claims, the phrase "sized and dimensioned to accommodate 0% shrinkage" is not intended to mean that 0% shrinkage occurs, but is rather intended to mean that the corresponding mold is not sized and dimensioned to accommodate anything other than 0% shrinkage. A mold that is "sized and dimensioned to accommodate 0% shrinkage is deliberately not sized and dimensioned to compensate for any shrinkage that may occur. That is, the corresponding mold is not designed to be any percentage larger than the intended final size of the molded structure despite the fact that some shrinkage of the molded structure may be expected to occur.

The shrunken first longitudinal section of elastomer may be removed from the first mold and deposited onto an inner surface of the second mold. With the first longitudinal section of elastomer having shrunken, depositing the first longitudinal section of elastomer onto an inner surface of the second mold may advantageously include stretching the first longitudinal section of elastomer onto the inner surface of the second mold. For example, the second mold may also be sized and dimensioned to accommodate 0% shrinkage of the second longitudinal section of elastomer and the first longitudinal section of elastomer may be stretched to its intended final size when deposited onto or against the inner surface of the second mold. With the first longitudinal section of elastomer stretched to its intended final size on/against an inner surface of the second mold, the flexible printed circuit board may be deposited onto/against the recessed surface of the first longitudinal section of elastomer and both the flexible printed circuit board and at least a portion of the first longitudinal section of elastomer may be overmolded with the second longitudinal section of elastomer. When the overmolded structure is removed from the second mold, any shrinkage of the first and/or second longitudinal section(s) of elastomer is limited by the flexible printed circuit board enclosed thereby and may be essentially evenly distributed if the same elastomer material is used for both the first and second longitudinal section. Such shrinkage can advantageously help secure the flexible printed board in place within the inner volume of the overmolded elastomer band.

A further aspect of method 500, in accordance with the present systems, articles, and methods, is the locations of the "gates" through which elastomer material is injected into a mold. The locations of the gates through which elastomer material is injected into the second mold is particularly influential because when the elastomer material is injected into the second mold it impinges upon a surface of the flexible printed circuit board (which is deposited upon/against the recessed surface of the first longitudinal section of elastomer) and can cause the flexible printed circuit board to slide, bunch, or otherwise become displaced relative to its original and/or intended position against the recessed surface of the first longitudinal section of elastomer. In accordance with the present systems, articles, and methods, a first gate of the second mold may be positioned at (or at least, proximate to) a first one of the number of semi-rigid changes in direction in the first longitudinal section of the elastomer band. See impression 370 in FIG. 3C for an example of this approximate position. From this position, elastomer material injected into the second mold through the gate initially impinges on the flexible printed circuit board at the vertex of the change in direction and then spreads along the two portions of the first longitudinal section that connect to that vertex. As the injected elastomer spreads from the gate, the flexible printed circuit board is pressed against the vertex of the change in direction and then gradually pressed down along the lengths of the two portions of the first longitudinal section that connect at that vertex. As previously described, a layer of pressure sensitive adhesive may be sandwiched in between the flexible printed circuit board and the recessed surface of the first longitudinal section of elastomer, and with the gate in this position the pressure sensitive adhesive may first be activated at the vertex of the change in direction to adhere/secure the flexible printed circuit board in position against the recessed surface of the first longitudinal section of elastomer at that vertex and then gradually activated to adhere/secure the flexible printed circuit board along the lengths of the portions of the first longitudinal section of elastomer that connect at that vertex.

For structures that employ multiple semi-rigid changes in direction (e.g., for cable 200 from FIG. 2 and cable 400 from FIGS. 4A, 4B and 4C), it can be advantageous for a plurality of additional gates to be employed in the second mold during injection of the elastomer material forming the second longitudinal section of elastomer, and for each gate in the plurality of additional gates to be positioned at a location of a respective one of the multiple semi-rigid changes in direction. In this way, elastomer material injected through each respective gate will bind the flexible printed circuit board to the respective vertices of the changes in direction and then spread along the length of the cable structure to meet/merge at the relatively straight portions in the length of the cable where stresses/strains are likely to be minimal during use.

In accordance with the present systems, articles, and methods, the restoring forces effected by changing the angle of a semi-rigidly set change in direction in an elastomer band may be gentler, and may grow less dramatically as the change in the angle is increased, compared to other sources of elasticity. For example, a straight elastic cable is known (in accordance with Hooke's Law) to exhibit linear elasticity meaning that the restoration force grows linearly as the length of the cable is stretched. The tortuous cables described herein can provide sub-linear elasticity so that the restoring force grows sub-linearly as the length of the cable is stretched. This is a further feature that renders the elastic electrical cables described herein particularly well-suited for use in wearable electronic devices. Returning to FIG. 1, a user with a particularly large forearm that causes adaptive couplers 111 and 112 to stretch to a large extent may nevertheless comfortably don device 100 because the tortuous nature of adaptive couplers 111 and 112 provides a sub-linear (or, ideally, near constant within the expected circumference range of device 100) restoring force such that device 100 feels "less tight" on the arm of such a user then, for example, a similar configuration that employed straight adaptive couplers with no semi-rigidly set changes in direction.

A further advantage of the band geometries described herein is that such geometries may provide substantially uniform compressive forces on the limb of the user upon which the band is worn (e.g., on the arm of the user) to enhance comfort and performance of on-board, contact-based sensors such as sensors 130. Likewise, such geometries may expand substantially uniformly to maintain uniform angular spacing between sensors 130 as described in U.S. Non-Provisional patent application Ser. No. 14/276, 575.

Throughout this specification and the appended claims, reference is often made to an "elastomer" material, such as an "elastomer band." The term elastomer is used to generally encompass polymers that exhibit viscoelasticity (such as thermosets and/or thermoplastics) but, in principle, elastomers are used only as examples herein and may be substituted by any material that likewise exhibits sufficient elasticity to apply the teachings of the present systems, articles, and methods in any particular application. Thermoplastics formulated by Dupont are used as non-limiting examples of elastomer materials in the present systems, articles, and methods. The composition of the elastomer material will influence the physical properties of the resulting molded structure. Composite materials may be used (e.g., including materials integrated into an elastomer, such as Kevlar®, textiles, laminate materials and/or filler materials), where the composition of the material may be selected to provide desired properties in the molded structure. For example, stiffeners may be added to the elastomer material either uniformly throughout, or at specific locations in the molded shape, to achieve uniform or localized isotropic (or anisotropic) control of the deformation properties of the molded structure. In a similar way, geometric features (e.g., mechanical flexures) may be incorporated into the design to influence the physical properties of the molded structure.

Depending on the specific application, either the same or different elastomer material(s) may be used at successive stages of a multi-shot overmold process in accordance with the present systems, articles, and methods. That is, in some applications a first shot (e.g., a first longitudinal section 301*a*) may be molded using a first elastomer material and a second shot (e.g., a second longitudinal section 301*b*) may be molded over at least a portion of the first shot using a second elastomer material.

The present systems, articles, and methods generally describe overmolded electric structures, and methods of manufacturing thereof, in which at least one overmolded electrically conductive pathway is a flexible electrically conductive pathway, such as a conductive trace on a flexible printed circuit board. Such flexibility is generally advantageous in application where a degree of elasticity in the overmolded electric structure is desired, such as in adaptive couplers of wearable electronic devices. However, the methods of manufacturing/fabricating overmolded electric structures described herein may generally be applied using substantially rigid electric structures, for example structures that are not required/desired to be elastic, or more generally in any electric device that includes at least one electrically conductive pathway. Specifically, rigid electronics and/or rigid printed circuit boards, with or without on-board discrete circuit components according to the application, may be at least partially contained in the inner volume of an elastomer material by using any or all of the techniques and methods of multi-stage overmolding described herein (except those aspects that are specifically described/claimed as involving flexible elements).

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors, central processing units, graphical processing units), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a processor-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the processor-readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application Ser. No. 61/940,048; U.S. Provisional Patent Application Ser. No. 62/031,651; U.S. Non-Provisional patent application Ser. No. 14/186,889; U.S. Non-Provisional patent application Ser. No. 14/194,252; U.S. Provisional Patent Application Ser. No. 61/866,960 (now U.S. Non-Provisional patent application Ser. No. 14/461,044); U.S. Provisional Patent Application Ser. No. 61/869,526 (now U.S. Non-Provisional patent application Ser. No. 14/465,194); U.S. Provisional Application Ser. No. 61/872,569 (now U.S. Non-Provisional patent application Ser. No. 14/471,982); U.S. Non-Provisional patent application Ser. No. 14/276,575; U.S. Provisional Application Ser. No. 61/909,786 (now U.S. Non-Provisional patent application Ser. No. 14/553,657); and U.S. Provisional Patent Application Ser. No. 61/915,338 (now U.S. Non-Provisional patent application Ser. No. 14/567,826), are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An annular wearable electronic device having a circumference that is variable in a dimension, the annular wearable electronic device comprising:
   a first pod structure positioned at least approximately on the circumference of the annular wearable electronic device, wherein the first pod structure includes electric circuitry;
   a second pod structure positioned at least approximately on the circumference of the annular wearable electronic device, wherein the second pod structure includes electric circuitry and wherein the first pod structure and the second pod structure are physically separated from one another by a first distance at least approximately along the circumference of the annular wearable electronic device; and
   a first adaptive coupler positioned at least approximately on the circumference of the annular wearable electronic device, wherein the first adaptive coupler provides both electrically conductive coupling and adaptive physical coupling between the first pod structure and the second pod structure, and wherein the first adaptive coupler comprises:
  at least a first electrically conductive pathway that is electrically conductively coupled to both the electric circuitry of the first pod structure and the electric circuitry of the second pod structure; and
  a first elastomer band that is physically coupled to both the first pod structure and the second pod structure, wherein at least a portion of the first electrically conductive pathway extends through an inner volume of the first elastomer band, and wherein a length of the first elastomer band that couples in between the first pod structure and the second pod structure is greater than the first distance and includes at least one semi-rigidly set change in direction.

2. The annular wearable electronic device of claim 1 wherein:
  when not worn by a user, the dimension of the circumference of the annular wearable electronic device is a minimum value with the first adaptive coupler in an unstretched state; and
  when worn by the user, the dimension of the circumference of the annular wearable electronic device is increased to encircle a portion of the user with the first adaptive coupler in a stretched state, the stretched state of the first adaptive coupler achieved by a change in an angle of the at least one semi-rigidly set change in direction in the length of the first elastomer band that couples in between the first pod structure and the second pod structure.

3. The annular wearable electronic device of claim 1 wherein the first elastomer band includes an overmold portion over the at least a portion of the first electrically conductive pathway that extends through the inner volume of the first elastomer band.

4. The annular wearable electronic device of claim 3 wherein the first elastomer band comprises:
  a first longitudinal section of elastomer having a recess that is sized and dimensioned to receive the at least a portion of the first electrically conductive pathway that extends through the inner volume of the first elastomer band, wherein the first longitudinal section of elastomer includes the number of semi-rigidly set changes in direction; and
  a second longitudinal section of overmold elastomer over at least a portion of the recess of the first longitudinal section of elastomer to define the inner volume of the first elastomer band.

5. The annular wearable electronic device of claim 1 wherein the first electrically conductive pathway includes at least one electrically conductive trace carried by a flexible substrate.

6. The annular wearable electronic device of claim 1, further comprising a third pod structure positioned at least approximately on the circumference of the annular wearable electronic device, wherein:
  the third pod structure includes electric circuitry;
  the second pod structure and the third pod structure are physically separated from one another by a second distance at least approximately along the circumference of the annular wearable electronic device;
  the first adaptive coupler provides electrically conductive coupling and adaptive physical coupling between the second pod structure and the third pod structure;
  the first adaptive coupler further comprises at least a second electrically conductive pathway that is electrically conductively coupled to the electric circuitry of the second pod structure and to the electric circuitry of the third pod structure; and
  the first elastomer band is physically coupled to both the second pod structure and the third pod structure, wherein at least a portion of the second electrically conductive pathway extends through an inner volume of the first elastomer band, and wherein a length of the first elastomer band that couples in between the second pod structure and the third pod structure is greater than the second distance and includes at least one semi-rigidly set change in direction.

7. The annular wearable electronic device of claim 1, further comprising:
  a third pod structure positioned at least approximately on the circumference of the annular wearable electronic device, wherein the third pod structure includes electric circuitry and wherein the second pod structure and the third pod structure are physically separated from one another by a second distance at least approximately along the circumference of the annular wearable electronic device; and
  a second adaptive coupler positioned at least approximately on the circumference of the annular wearable electronic device, wherein the second adaptive coupler provides both electrically conductive coupling and adaptive physical coupling between the second pod structure and the third pod structure, and wherein the second adaptive coupler comprises:
  at least a second electrically conductive pathway that is electrically conductively coupled to both the electric circuitry of the third pod structure and the electric circuitry of the second pod structure; and
  a second elastomer band that is physically coupled to both the second pod structure and the third pod structure, wherein at least a portion of the second electrically conductive pathway extends through an inner volume of the second elastomer band, and wherein a length of the second elastomer band that couples in between the second pod structure and the third pod structure is greater than the second distance and includes at least one semi-rigidly set change in direction.

8. The annular wearable electronic device of claim 1 wherein the length of the first elastomer band that couples in between the first pod structure and the second pod structure follows a tortuous path that includes the at least one semi-rigidly set change in direction.

9. The annular wearable electronic device of claim 1, further comprising:
  a second elastomer band that is physically coupled to both the first pod structure and the second pod structure, wherein a length of the second elastomer band that couples in between the first pod structure and the second pod structure is greater than the first distance and includes at least one semi-rigidly set change in direction.

10. An elastic electrical cable comprising:
  a flexible printed circuit board including at least one electrically conductive trace carried on a flexible substrate; and
  an elastomer band, wherein at least a portion of the flexible printed circuit board extends through an inner volume of the elastomer band, and wherein a length of the elastomer band follows a tortuous path that includes a number of semi-rigidly set changes in direction.

11. The elastic electrical cable of claim 10 wherein the elastomer band includes an overmold portion over the at least a portion of the flexible printed circuit board that extends through the inner volume of the elastomer band.

12. The elastic electrical cable of claim 11 wherein the elastomer band comprises:
   a first longitudinal section of elastomer having a recess that is sized and dimensioned to receive the at least a portion of the flexible printed circuit board, wherein the first longitudinal section of elastomer includes the number of semi-rigidly set changes in direction; and
   a second longitudinal section of overmold elastomer over at least a portion of the first longitudinal section of elastomer to define the inner volume of the band.

13. The elastic electrical cable of claim 10 wherein a first end of the flexible printed circuit board is positioned proximate a first end of the elastomer band and a second end of the flexible printed circuit board is positioned proximate a second end of the elastomer band, and wherein the elastic electrical cable further comprises:
   a first electrical connector electrically conductively coupled to the first end of the flexible printed circuit board; and
   a second electrical connector electrically conductively coupled to the second end of the flexible printed circuit board.

14. The elastic electrical cable of claim 10 wherein the elastomer band includes an impression from an injection gate, the impression positioned at one of the number of semi-rigidly set changes in direction in correspondence with the position of the injection gate in a mold used to form the elastomer band.

15. The elastic electrical cable of claim 14, further comprising an adhesive layer that adheres a first surface of the flexible printed circuit board to an inner surface of the elastomer band.

16. A method of fabricating an elastic electrical cable, wherein the elastic electrical cable comprises a flexible printed circuit board and an elastomer band, and wherein at least a portion of the flexible printed circuit board extends through an inner volume of the elastomer band, the method comprising:
   molding a first longitudinal section of the elastomer band to include a recessed surface and a number of semi-rigid changes in direction;
   depositing the flexible printed circuit board against the recessed surface of the first longitudinal section of the elastomer band; and
   overmolding at least a portion of the flexible printed circuit board and at least a portion of the first longitudinal section of the elastomer band with a second longitudinal section of the elastomer band to enclose at least a portion of the flexible printed circuit board within the inner volume of the elastomer band.

17. The method of claim 16 wherein depositing the flexible printed circuit board against the recessed surface of the first longitudinal section of the elastomer band includes:
   bending the flexible printed circuit board to match the number of semi-rigid changes in direction in the first longitudinal section of the elastomer band; and
   positioning the bent flexible printed circuit board against the recessed surface of the first longitudinal section of the elastomer band.

18. The method of claim 16 wherein molding a first longitudinal section of the elastomer band includes molding the first longitudinal section of the elastomer band in a first mold, and wherein overmolding at least a portion of the flexible printed circuit board and at least a portion of the first longitudinal section of the elastomer band with a second longitudinal section of the elastomer band includes overmolding at least a portion of the flexible printed circuit board and at least a portion of the first longitudinal section of the elastomer band with a second longitudinal section of the elastomer band in a second mold.

19. The method of claim 18, further comprising:
   removing the first longitudinal section of the elastomer band from the first mold; and
   depositing the first longitudinal section of the elastomer band against an inner surface of the second mold, wherein depositing the flexible printed circuit board against the recessed surface of the first longitudinal section of the elastomer band includes depositing the flexible printed circuit board against the recessed surface of the first longitudinal section of the elastomer band while the first longitudinal section of the elastomer band is against the inner surface of the second mold.

20. The method of claim 19 wherein the first mold is sized and dimensioned to accommodate substantially 0% shrinkage of the first longitudinal section of the elastomer band, and wherein:
   molding a first longitudinal section of the elastomer band includes molding a first longitudinal section of the elastomer band to accommodate substantially 0% shrinkage of the first longitudinal section of the elastomer band; and
   depositing the first longitudinal section of the elastomer band against an inner surface of the second mold includes stretching the first longitudinal section of the elastomer band against the inner surface of the second mold.

21. The method of claim 20 wherein the second mold is sized and dimensioned to accommodate substantially 0% shrinkage of the second longitudinal section of the elastomer band, and wherein overmolding at least a portion of the flexible printed circuit board and at least a portion of the first longitudinal section of the elastomer band with a second longitudinal section of the elastomer band includes overmolding at least a portion of the flexible printed circuit board and at least a portion of the first longitudinal section of the elastomer band with a second longitudinal section of the elastomer band to accommodate substantially 0% shrinkage of the second longitudinal section of the elastomer band while the first longitudinal section of the elastomer band is stretched against the inner surface of the second mold.

22. The method of claim 16, further comprising:
   depositing an adhesive on a first surface of the flexible printed circuit board, and wherein depositing the flexible printed circuit board against the recessed surface of the first longitudinal section of the elastomer band includes depositing the first surface of the flexible printed circuit board against the recessed surface of the first longitudinal section of the elastomer band after depositing the adhesive on the first surface of the flexible printed circuit board.

23. The method of claim 22 wherein the adhesive includes a pressure sensitive adhesive, and further comprising pressing the flexible printed circuit board against the recessed surface of the first longitudinal section of the elastomer band, wherein pressing the flexible printed circuit board against the recessed surface of the first longitudinal section of the elastomer band activates the pressure sensitive adhesive and adheres the first surface of the flexible printed circuit board to the recessed surface of the first longitudinal section of the elastomer band.

24. The method of claim 16 wherein overmolding at least a portion of the flexible printed circuit board and at least a portion of the first longitudinal section of the elastomer band with a second longitudinal section of the elastomer band includes injecting an elastomer material into a mold through a first gate, the first gate positioned at a location of a first one of the number of semi-rigid changes in direction in the first longitudinal section of the elastomer band.

25. The method of claim 24 wherein overmolding at least a portion of the flexible printed circuit board and at least a portion of the first longitudinal section of the elastomer band with a second longitudinal section of the elastomer band includes injecting the elastomer material into the mold through a plurality of additional gates, each gate in the plurality of additional gates positioned at a location of a respective one of the number of semi-rigid changes in direction in the first longitudinal section of the elastomer band.

26. An elastic electrical cable that includes a flexible printed circuit board and an elastomer band, the elastic electrical cable prepared by a process comprising the steps of:
   molding a first longitudinal section of the elastomer band to include a recessed surface and a number of semi-rigid changes in direction;
   depositing the flexible printed circuit board onto the recessed surface of the first longitudinal section of the elastomer band; and
   overmolding the flexible printed circuit board and at least a portion of the first longitudinal section of the elastomer band with a second longitudinal section of the elastomer band to enclose at least a portion of the flexible printed circuit board within an inner volume of the elastomer band.

27. A method of fabricating an electric device, wherein the electric device comprises at least an electrically conductive pathway and an elastomer band, and wherein at least a portion of the electrically conductive pathway extends through an inner volume of the elastomer band, the method comprising:
   molding a first longitudinal section of the elastomer band in a first mold that is sized and dimensioned to accommodate substantially 0% shrinkage of the first longitudinal section of the elastomer band;
   removing the first longitudinal section of the elastomer band from the first mold;
   stretching the first longitudinal section of the elastomer band against an inner surface of a second mold;
   depositing the electrically conductive pathway against the first longitudinal section of the elastomer band while the first longitudinal section of the elastomer band is stretched against the inner surface of the second mold; and
   overmolding at least a portion of the electrically conductive pathway and at least a portion of the first longitudinal section of the elastomer band with a second longitudinal section of the elastomer band in a second mold to enclose at least a portion of the electrically conductive pathway within the inner volume of the elastomer band.

28. The method of claim 27 wherein the second mold is sized and dimensioned to accommodate substantially 0% shrinkage of the second longitudinal section of the elastomer band, and wherein overmolding at least a portion of the electrically conductive pathway and at least a portion of the first longitudinal section of the elastomer band with a second longitudinal section of the elastomer band includes overmolding at least a portion of the electrically conductive pathway and at least a portion of the first longitudinal section of the elastomer band with a second longitudinal section of the elastomer band to accommodate substantially 0% shrinkage of the second longitudinal section of the elastomer band while the first longitudinal section of the elastomer band is stretched against the inner surface of the second mold.

\* \* \* \* \*